(12) United States Patent
Cui et al.

(10) Patent No.: US 9,080,186 B2
(45) Date of Patent: Jul. 14, 2015

(54) COMPOSITIONS COMPRISING CATIONIC AMPHIPHILES AND COLIPIDS FOR DELIVERING THERAPEUTIC MOLECULES

(75) Inventors: Kunyuan Cui, Bothell, WA (US); Dong Liang, Everett, WA (US)

(73) Assignee: Agave Pharma, Incorporated, Seattle, WA (US)

( * ) Notice: Subject to any disclaimer, the term of this patent is extended or adjusted under 35 U.S.C. 154(b) by 0 days.

(21) Appl. No.: 13/320,901

(22) PCT Filed: May 16, 2010

(86) PCT No.: PCT/US2010/035049
§ 371 (c)(1),
(2), (4) Date: Jul. 9, 2012

(87) PCT Pub. No.: WO2010/135207
PCT Pub. Date: Nov. 25, 2010

(65) Prior Publication Data
US 2012/0289584 A1    Nov. 15, 2012

Related U.S. Application Data

(60) Provisional application No. 61/178,962, filed on May 16, 2009.

(51) Int. Cl.
| *A61K 51/00* | (2006.01) |
| *A61K 36/14* | (2006.01) |
| *A61K 48/00* | (2006.01) |
| *C12N 15/88* | (2006.01) |
| *C12N 15/87* | (2006.01) |
| *A61K 9/00* | (2006.01) |
| *A61K 9/127* | (2006.01) |
| *A61K 9/14* | (2006.01) |
| *A61K 47/48* | (2006.01) |

(52) U.S. Cl.
CPC .............. *C12N 15/88* (2013.01); *A61K 9/0014* (2013.01); *A61K 9/0019* (2013.01); *A61K 9/1272* (2013.01); *A61K 9/145* (2013.01); *A61K 47/48815* (2013.01)

(58) Field of Classification Search
CPC ... C12N 15/88; A61K 9/0019; A61K 9/0014; A61K 9/1272; A61K 9/145
See application file for complete search history.

(56) References Cited

U.S. PATENT DOCUMENTS

| 4,511,069 A | 4/1985 | Kalat |
| 4,778,810 A | 10/1988 | Wenig et al. |
| 5,208,036 A | 5/1993 | Eppstein et al. |
| 5,264,618 A | 11/1993 | Felgner et al. |
| 5,279,833 A | 1/1994 | Rose |
| 5,283,185 A | 2/1994 | Epand et al. |
| 5,753,613 A | 5/1998 | Ansell et al. |
| 5,767,099 A | 6/1998 | Harris et al. |
| 5,785,992 A | 7/1998 | Ansell et al. |
| 5,849,902 A | 12/1998 | Arrow et al. |
| 5,948,767 A | 9/1999 | Scheule et al. |
| 6,331,524 B1 * | 12/2001 | Scheule et al. ............... 514/44 R |
| 7,982,027 B2 * | 7/2011 | MacLachlan et al. ........ 536/24.5 |
| 8,598,333 B2 * | 12/2013 | MacLachlan et al. ........ 536/24.5 |
| 2001/0044147 A1 * | 11/2001 | Sullivan et al. ............. 435/320.1 |
| 2002/0102297 A1 | 8/2002 | Safinya et al. |
| 2005/0175682 A1 | 8/2005 | Heyes et al. |
| 2006/0083780 A1 | 4/2006 | Heyes et al. |
| 2006/0240093 A1 * | 10/2006 | MacLachlan et al. ......... 424/450 |
| 2007/0172950 A1 * | 7/2007 | Wheeler et al. ............... 435/458 |
| 2008/0299177 A1 | 12/2008 | Hardy |

FOREIGN PATENT DOCUMENTS

| JP | 2002-524473 A | 8/2002 |
| WO | WO 92/07065 | 4/1992 |
| WO | WO 93/15187 | 8/1993 |
| WO | WO 96/10390 | 4/1996 |
| WO | WO 00/14262 A2 | 3/2000 |
| WO | WO 02/087541 | 11/2002 |
| WO | WO 2011/084721 | 7/2011 |

OTHER PUBLICATIONS

Hayes, et al. (2006) "Genospheres: self-assembling nucleic acid-lipid nanoparticles suitable for targeted gene delivery", Gene Therapy, 13: 646-51.*
U.S. Appl. No. 08/316,399, filed Sep. 30, 1994, Ansell et al.
Gold, et al., "Diversity of oligonucleotide functions", Annu. Rev. Biochem., Jul. 1995, 64, 763-797.
Hermann and Patel, "Adaptive recognition by nucleic acid aptamers", Science, Feb. 2000, 287(5454), 820-825.
International Patent Application No. PCT/US2010/035049: International Search Report and Written Opinion dated Aug. 4, 2010, 11 pages.
Jayasena, "Aptamers: An emerging class of molecules that rival antibodies in diagnostics", Clinical Chemistry, Sep. 1999, 45(9), 1628-1650.
Limbach, et al., "Summary: the modified nucleosides of RNA", Nucleic Acids Res., Jun. 1994, 22(12), 2183-2196.
European Patent Application No. 10778182.5: Communication and European Search Report dated Nov. 12, 2013, 10 pages.

(Continued)

*Primary Examiner* — Robert M Kelly
(74) *Attorney, Agent, or Firm* — Baker & Hostetler LLP

(57) ABSTRACT

This disclosure provides compositions consisting of solid mixture of cationic lipids and a polynucleotide, wherein the cationic lipid molecules form a water-insoluble ionic complex with the polynucleotide. What is also described is an anhydrous mixture of the cationic lipids and the polynucleotide solubilized in an organic or polar aprotic solvent. The anhydrous compositions are useful in preparing therapeutic formulations and in the diagnosis and treatment of diseases and conditions. The compositions are useful for delivery of agents such as nucleic acid therapeutics to cells, tissues, organs, and subjects.

22 Claims, 7 Drawing Sheets

(56) References Cited

OTHER PUBLICATIONS

Leal et al., "Local and Translational Dynamics in DNA-Lipid Assemblies Monitored by Solid-State and Diffusion NMR", Biochimica et Biophysica Acta, 2008, 1778, 214-228.

Mel'nikov et al., "Solubilization of DNA-Cationic Lipid Complexes in Hydrophobic Solvents. A Single-Molecule Visualization by Fluorescence Microscopy", Langmuir, 1999, 15, 1923-1928.

Neumann et al., "Reversible Structural Switching of a DNA-DDAB Film", Journal of American Chemical Society, Mar. 18, 2009, 131(10), 3440-3441.

Okahata et. al.; "Anisotropic Electric Conductivity in an Aligned DNA Cast Film"; Journal of the American Chemical Society; Jun. 24, 1998; vol. 120 No. 24; p. 6165-6166.

\* cited by examiner

US 9,080,186 B2

COMPOSITIONS COMPRISING CATIONIC AMPHIPHILES AND COLIPIDS FOR DELIVERING THERAPEUTIC MOLECULES

CROSS-REFERENCE TO RELATED APPLICATIONS

This application is the National Stage of International Application No. PCT/US2010/035049 filed May 16, 2010, which claims the benefit of U.S. Provisional Application No. 61/178,962, filed May 16, 2009, the disclosures of which are incorporated herein by reference in their entireties.

TECHNICAL FIELD

What is described is a storage-stable salt of a nucleic acid and a cationic lipid, and a method of using this salt to prepare lipid formulations for delivery of nucleic acid to tissue cells when administered to a mammal.

BACKGROUND

A number of different types of nucleic acids are currently being developed as therapeutics for the treatment of a number of diseases. These nucleic acids include DNA in gene therapy, plasmids-based interfering nucleic acids, small interfering nucleic acids for use in RNA interference (RNAi), including siRNA, miRNA, antisense molecules, ribozymes and aptamers. As these molecules are being developed, there has been developed a need to produce them in a form that is stable and has a long shelf-life and that can be easily incorporated into an anhydrous organic or anhydrous polar aprotic solvent to enable encapsulations of the nucleic acids without the side-reactions that can occur in a polar aqueous solution or a nonpolar solvents.

The present invention relates to novel lipid compositions that facilitate the intracellular delivery of biologically active and therapeutic molecules. The present invention relates also to pharmaceutical compositions that comprise such lipid compositions, and that are useful to deliver therapeutically effective amounts of biologically active molecules into the cells of patients.

The delivery of a therapeutic compound to a subject is important for its therapeutic effects and usually it can be impeded by limited ability of the compound to reach to targeted cells and tissues. Improvement of such compounds to enter the targeted cells of tissues by a variety of the means of delivery is crucial. The present invention relates the novel lipids, a compositions and method for preparation that facilitate the targeted intracellular delivery of biological active molecules.

Examples of biologically active molecules for which effective targeting to a patient's tissues is often not achieved include: (1) numerous proteins including immunoglobin proteins, (2) polynucleotides such as genomic DNA, cDNA, or mRNA (3) antisense polynucleotides; and (4) many low molecular weight compounds, whether synthetic or naturally occurring, such as the peptide hormones and antibiotics.

One of the fundamental challenges now facing medical practitioners is that a number of different types of nucleic acids are currently being developed as therapeutics for the treatment of a number of diseases. These nucleic acids include DNA in gene therapy, plasmids small interfering nucleic acids (iNA) for use in RNA interference (RNAi), antisense molecules, ribozymes, antagomirs, microRNA and aptamers. As these nucleic are being developed, there is a need to produce lipid formulations that are easy to make and can be readily delivered to a target tissue.

SUMMARY

One aspect of the invention is a composition consisting of solid mixture of cationic lipids and a polynucleotide, wherein the cationic lipid molecules form a water-insoluble ionic complex with the polynucleotide (referred to hereinafter as the lipid/nucleic acid salt). An embodiment is one in which the molar ratio of cationic lipids to nucleotide monomers of the polynucleotide in the lipid/nucleic acid salt is between 0.1 and 10, preferably between 0.5 and 2. An embodiment of the invention is the lipid/nucleic acid salt in which the cationic lipid is selected from the group consisting of N,N-dioleyl-N,N-dimethylammonium chloride (DODAC); N-(1-(2,3-dioleyloxy)propyl)-N,N,N-trimethylammonium chloride (DOTMA); N,N-dimethyl-(2,3-dioleyloxy)propylamine ("DODMA"); N,N-distearyl-N,N-dimethylammonium bromide ("DDAB"); N-(1-(2,3-dioleoyloxy)propyl)-N,N,N-trimethylammonium chloride ("DOTAP"); 3-(N—(N',N'-dimethylaminoethane)-carbamoyl)cholesterol (DC-Chol); N-(1,2-dimyristyloxyprop-3-yl)-N,N-dimethyl-N-hydroxyethyl ammonium bromide ("DMRIE"); 1,2-Dilinoleyloxy-N,N-dimethylaminopropane (DLinDMA); and 1,2-Dilinolenyloxy-N,N-dimethylaminopropane (DLenDMA), dioctadecyldimethylammonium (DODMA), distearyldimethylammonium (DSDMA), 1,2-dilinoleyloxy-N,N-dimethylaminopropane (DLinDMA), 1,2-dilinolenyloxy-N,N-dimethylaminopropane (DLenDMA), $N^4$-spermine cholesteryl carbamate (GL-67), $N^4$-spermidine cholestryl carbamate (GL-53), 1-($N^4$-spermine)-2,3-dilaurylglycerol carbamate (GL-89) and mixtures thereof. Most preferably, the lipid is selected from the group consisting of DOTAP, DODAP, DLinDMA, DC-Chol, and DOTMA. Another aspect of the invention is the lipid/nucleic acid salt in which the nucleic acid is selected from the group consisting of DNA, RNA, antisense, aptamer, antagamer, plasmid-based interfering nucleic acid (iNA), ribozyme, small interfering nucleic acid (siRNA), microRNA (miRNA), and mixtures thereof. Preferably, the lipid/nucleic acid salt is in the form of an anhydrous solid, i.e., one in which water has been removed in vacuo or by drying under a stream of air, preferably nitrogen gas.

Another aspect of the invention is the lipid/nucleic acid salt which is made by a process of combining a cationic lipid with a polynucleotide in an aqueous solvent, producing a water-insoluble precipitate, isolating the precipitate, and drying the precipitate. One embodiment is the lipid/nucleic acid salt that is capable of being solubilized in an organic or polar aprotic solvent.

Another aspect of the invention is a solution comprising the lipid/nucleic acid salt dissolved in an organic or aprotic solvent ("the solution").

An embodiment is the solution, further comprising a carbamate, preferably a carbamate selected from the group consisting of N 6-tetrakis(3-aminopropyl)-1,3-propanediamine cholesteryl carbamate, N4-spermine cholesteryl carbamate, N4-spermidine cholesteryl carbamate, 1-(N4-spermine)-2,3-dilaurylglycerol carbamate, and 2,3-dioleyloxy-N-[2(sperminecarboxamido)ethyl]-N,N-dimethyl-1-propanamonium trifluoroacetate.

Another embodiment is the solution, further comprising a neutral phospholipid, preferably a phospholipid selected from the group consisting of phosphatidyl ethanolamine, phosphatidyl cocaine, phosphatidyl inositol, sphinogomyelin, and diphosphatidyl glycerol, and preferably a phospholipid comprised of 8-22 carbon alkyl chains, most preferably chains selected from a group consisting of 18:2, 20:4, and 22:6 alkyl chains.

Another embodiment is the solution, further comprising a sterol, preferably a sterol selected from the group consisting of cholesterol, lanosterol, 24-isopropylcholesterol, nicasterol, 7-dehydrocholesterol, 24-dehydrocholesterol, gorgosterol, dinosterol, 24S-hydroxycholesterol, a phytosterol, ergosterol, stigmasterol, campesterol, fucosterol, β-sitosterol, a phytostanol, a sterol ester, a steryl glycoside, and a steryl alkyl ether.

Another embodiment is the solution, further comprising a lipid-PEG compound, preferably wherein the lipid is a phospholipid or a sterol, and preferably having a PEG with a molecular weight between 200 and 5000 kDa.

Another aspect of the invention is a solution further comprising the solution with one or more lipids selected from the group consisting of cholesterol, polyethylene glycol (PEG) linked cholesterol (1K), phospholipid, and N 6-tetrakis(3-aminopropyl)-1,3-propanediamine cholesteryl carbamate. An embodiment is the solution in which phosphatidylethanolamine consists of a 8-24 alkyl chain with or without unsaturated bonds. Another embodiment is the solution further comprising a variety of ratios of above compositions, preferably, 1 part polynucleotide/4.4 parts N 6-tetrakis(3-aminopropyl)-1,3-propanediamine cholesteryl carbamate/4.4 parts phosphatidylethanolamine/14.4 parts cholesterol PEG/1.6 parts cholesterol (weight/weight). Another embodiment is the solution further comprising 1 part polynucleotide/8.8 parts N 6-tetrakis(3-aminopropyl)-1,3-propanediamine cholesteryl carbamate/2.2 parts phosphatidylethanolamine/14.4 parts cholesterol PEG/1.6 parts cholesterol (weight/weight). Another embodiment is the solution further comprising 1 part polynucleotide/6.6 parts N 6-tetrakis(3-aminopropyl)-1,3-propanediamine cholesteryl carbamate/2.2 parts phosphatidylethanolamine/14.4 parts cholesterol PEG/1.6 parts cholesterol (weight/weight). Another embodiment is the solution further comprising 1 part polynucleotide/4.4 parts N 6-tetrakis(3-aminopropyl)-1,3-propanediamine cholesteryl carbamate/4.4 parts phosphatidylethanolamine/21.6 parts cholesterol PEG/4.8 parts cholesterol (weight/weight).

Another aspect of the invention is the solution further comprising 1,2-dioleoyl-sn-glycero-3-phosphoethanolamine, cholesterol, and C16 PEG750 ceramide.

Another aspect of the invention is the solution further comprising 1,2-dilinoleoyl-sn-glycero-3-phosphoethanolamine, cholesterol, and a lipid-PEG selected from the group consisting of DSPE-PEG, DOPE-PEG, cholesterol-PEG.

Another aspect of the invention is any of the above solutions suitable for delivery of nucleic acid to skin.

Another aspect of the invention is a solid formulation obtained by removing the solvent from any of the solutions described above.

Another aspect of the invention is an aqueous formulation obtained by removing the solvent from any of the solutions described above and suspending the resulting solid in an aqueous solution, preferably to produce a solution suitable for administering to a subject, most preferably suitable for injection.

Another aspect of the invention is any of the above formulations suitable for delivery of a therapeutic molecule to the liver, to the lung or to a tumor.

DETAILED DESCRIPTION OF ILLUSTRATIVE EMBODIMENTS

Figure 1:
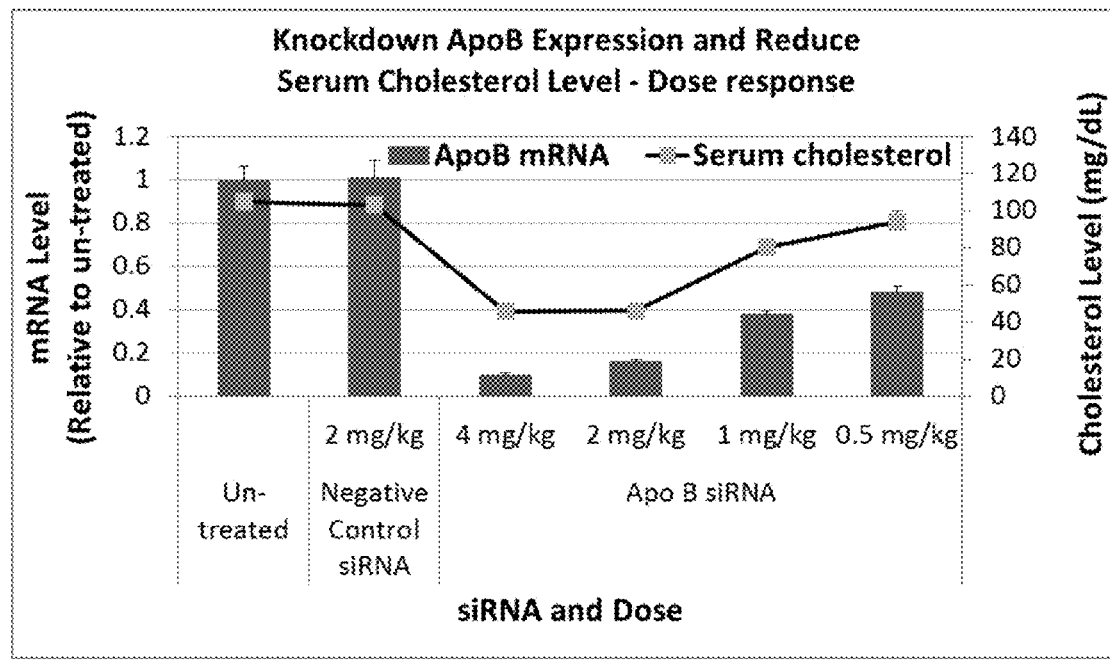
FIG. 1. This shows a dose-response curve of liver (ApoB) siRNA delivery formulations. Balb/C mice were administered a single dose of 0.2 ml formulated ApoB siRNA intravenously at the indicated dose level. The liver was harvested two days post injection for analyzing gene expression with real time RT-PCR method (GAPDH as reference gene). Serum was also harvested for analyzing total cholesterol level. Each data point represents the mean+SEM (n=6). The ApoB gene knockdown in mouse liver is correlated to serum cholesterol level changes FIG. 2. This shows a time course study on ApoB gene expression and corresponding cholesterol reduction in Balb/C mice were administered with a single dose of formulated siRNA intravenously at dosing volume of 0.2 ml/mouse and 2 mg/kg. At the limited time point, the liver tissue was harvested for analyzing gene expression as described above. The gene knockdown in liver and cholesterol change in serum almost last three weeks.

The present invention satisfies these needs and fulfills additional objects and advantages by providing novel methods and compositions that employ a nucleic acid with an organic counter-ion.

The present invention further fills this need by providing for organic counter ion nucleic acid salts in a non water soluble and stable form, in particular organic salts-interfering nucleic acid. These non water soluble precipitates are produced by bringing into contact a solution of an organic cation, that is, a positive charged compound with hydrophobic/lipophilic group, including, but not limited to, organic compounds containing protonated organic amines as cations, such as cationic lipids and procaine with an aqueous solution of nucleic acid under conditions wherein the cationic lipid molecules complex with the nucleic acid to form a cationic compound-nucleic acid precipitate. Precipitation occurs for cationic organic molecules with a carbon number or a sufficient degree of hydrophobicity to render the nucleic acid insoluble in water. The resulting precipitate contains an amount of the cationic lipid molecular positive charge in a one to one charge molar concentration with the number of nucleotides present in the nucleic acid. A less than one to one charge molar concentration with the number of nucleotides present in the nucleic acid will also be used for partial nucleic acid precipitation. The nucleic acid-organic cationic lipid precipitate can be recovered from the aqueous liquors using filtration, centrifugation and other methods available to those skilled in the art of chemical and physical process. The precipitated cationic lipid salt can be dried and subjected to numerous mechanical treatments to render it suitable for incorporation into solid and liquid dosage forms of nucleic drug formulations. It has surprisingly been determined that the water insoluble organic precipitate of nucleic acid of certain organic cations can be readily solvated in many common organic solvents including solvents that are of the polar aprotic class (dimethylacetamide, dimethylformamide, N-methyl pyrrolidine, diglyme and other ether glycols, chloroform, methylene chloride and other halogenated organic solvents, tetrahydrofuran and other cyclic ether solvents), these solvents can be employed under anhydrous conditions and are of industrial value for the use in chemical transformation and reaction of reagents into new chemical forms.

Those skilled in the art will readily understand that the nucleic acid precipitates when solvated in an anhydrous, aprotic solvent, can be contacted by numerous reactive intermediates to transform the nucleic acid by chemical reaction into new forms of nucleic acids. These reactions include but are not limited to acylations of primary and secondary alcohols on the ribose and dexyribose sugars to attach fluorescent probes or reporter molecules, methylation chemistry to convert ribose nucleic acids into nuclease resistant 2'O-methylated ribose nucleic acids, amidation of the exocyclic amino groups of uracil, thymine, cytosine, adenine and guanine to protect the reactive free amino groups of the nucleic acids. The chemical modification of terminal primary hydroxyl groups is envisioned as a very facile reaction and can be used to couple cholesterol and other hydrophobic entities into the nucleic acid polymers for therapeutic drug and gene delivery applications. The utility of this method can be extended to the recovery and chemical modification of the minor constituents of natural ribosides including inosine and many modified RNA nucleosides found in transfer ribonucleic acids. The chemical transformations can affect new physical and chemical properties such as increased resistance to chemical and enzymatic degradation, organ, tissue and cell specific diseased targeting and increase the value of the nucleic acid for other pharmaceutical and industrial applications.

Contacting the nucleic acid solution with the solution of cationic lipids is accomplished by mixing together a first solution of nucleic acids, which is typically an aqueous solution, with a solution of the cationic lipids. The cationic lipid can be in solution in either an organic or aqueous solvent. One of skill in the art will understand that this mixing can take place by any number of methods, for example by mechanical means such as by using vortex mixers or injection pumps and stirred reactors.

Examples of cationic lipids that can be used in creating the cationic lipid nucleic acid salts include any of a number of lipid species that carry a net positive charge at a selected pH, such as physiological pH, (e.g., pH of about 7.0). As used herein, physiological pH refers to the pH of a biological fluid such as blood or lymph as well as the pH of a cellular compartment such as an endosome, an acidic endosome, or a lysosome). Such lipids include, but are not limited to, N,N-dioleyl-N,N-dimethylammonium chloride ("DODAC"); N-(1-(2,3-dioleyloxy)propyl)-N,N,N-trimethylammonium chloride ("DOTMA); N,N-dimethyl-(2,3-dioleyloxy)propylamine ("DODMA"); N,N-distearyl-N,N-dimethylammonium bromide ("DDAB"); N-(1-(2,3-dioleoyloxy)propyl)-N,N,N-trimethylammonium chloride ("DOTAP"); 3-(N—(N', N'-dimethylaminoethane)-carbamoyl)cholesterol ("DC-Chol"); N-(1,2-dimyristyloxyprop-3-yl)-N,N-dimethyl-N-hydroxyethyl ammonium bromide ("DMRIE"); 1,2-Dilinoleyloxy-N,N-dimethylaminopropane (DLinDMA); and 1,2-Dilinolenyloxy-N,N-dimethylaminopropane (DLenDMA). The following lipids are cationic and have a positive charge at below physiological pH: 1,2-dimyristoyl-3-dimethylammonium propane (DODAP), DODMA, DMDMA and the like. These lipids and related analogs have been described in copending U.S. Ser. No. 08/316,399; U.S. Pat. Nos. 5,208,036, 5,264,618, 5,279,833 and 5,283,185. Additionally, a number of commercial preparations of cationic lipids are available and can be used in the present invention. Except the cationic lipids, any organic cations carrying the positive charge can potentially be used for the nucleic acid precipitation and used the same.

The organic cations that can be used in creating the cation-nucleic acid precipitates can be in either aqueous to form the micelle or in alcohol in a solubilized state or in the mixture of both aqueous and alcohol. In some case the organic cations are also in other organic solution, such as chloroform, to mix with aqueous solution containing nucleic acid. After the evaporation of organic solvents the precipitates will be formed.

This disclosure provides pharmaceutically acceptable nucleic acid compositions useful for therapeutic delivery of nucleic acids, plasmids, siRNA, miRNA, antisense nucleic acids, ribozymes, aptamers, antagomirs and gene-silencing nucleic acid and the like. These compositions and methods may be used for prevention and/or treatment of diseases in a mammal. The cationic lipid nucleic acid salts of the present invention results in cationic nucleic acid salts having dramatically improved solubility in organic solvents such as dichloromethane, chloroform, THF, 1-octanol and many biologically compatible solvents such as DMSO, dimethylacetamide, lauroyl glycol and other oily vehicles such as isopropyl myristate, oleic esters, methyl, ethyl, isopropyl, and higher alkyl substituents.

These cationic lipid nucleic acid salts can then be re-suspended in an organic solvent and upon mixing with other lipids produce nucleic acid lipid complexes that can be administered to an individual for gene therapies using plasmid DNA as the nucleic acid, or for down-regulating a gene using antisense, siRNA, miRNA, ribozymes, or to inhibit other conditions using aptamers as the nucleic acid.

DEFINITIONS

Definitions of technical terms provided herein should be construed to include without recitation those meanings associated with these terms known to those skilled in the art, and are not intended to limit the scope of the invention.

The use herein of the terms "a," "an," "the," and similar terms in describing the invention, and in the claims, are to be construed to include both the singular and the plural. The terms "comprising," "having," "including," and "containing" are to be construed as open-ended terms which mean, for example, "including, but not limited to." Recitation of a range of values herein refers individually to each and any separate value falling within the range as if it were individually recited herein, whether or not some of the values within the range are expressly recited. Specific values employed herein will be understood as exemplary and not to limit the scope of the invention.

The term "organic cation" and "cationic lipid" refers to any of a number of lipid species or organic compound that carry a net positive charge at a selected pH, such as physiological pH (e.g., pH of about 7.0). A number of cationic lipids and related analogs, which are also useful in the present invention, have been described in U.S. Patent Publication No. 20060083780; U.S. Pat. Nos. 5,208,036; 5,264,618; 5,279,833; 5,283,185; 5,753,613; U.S. Pat. Nos. 5,767,099 and 5,785,992; and PCT Publication No. WO 96/10390. Examples of cationic lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 1,2-dilinoleyloxy-N,N-dimethylaminopropane (DLinDMA), 1,2-dilinolenyloxy-N,N-dimethylaminopropane (DLenDMA), $N^4$-spermine cholesteryl carbamate (GL-67), $N^4$-spermidine cholestryl carbamate (GL-53), 1-($N^4$-spermind)-2,3-dilaurylglycerol carbamate (GL-89) and mixtures thereof. As a non-limiting example, cationic lipids that have a positive charge below physiological pH include, but are not limited to, 1,2-dimyristoyl-3-dimethylammonium propane (DODAP), DODMA, and DSDMA. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA. The cationic lipid may be, e.g., DODAC, DDAB, DOTAP, DOTMA, DODMA, DLinDMA, DLenDMA, or mixtures thereof. Cationic lipids which are useful in the present invention can be any of a number of lipid species which carry a net positive charge at physiological pH. Such lipids include, but are not limited to, DODAC, DODMA, DSDMA, DOTMA, DDAB, DOTAP, DOSPA, DOGS, DC-Chol, DMRIE, and mixtures thereof. Additionally, a number of commercial preparations of cationic lipids are available and can be used in the present invention.

As used herein, the term interfering nucleic acid (iNA) refers to a nucleic acid duplexes having a sense and antisense strand, which when entered into a RISC complex induces enzymatic degradation of mRNA. Generally each strand contains predominantly RNA nucleotides but the strands can contain RNA analogs, RNA and RNA analogs, RNA and DNA, RNA analogs and DNA, or one strand that is completely DNA and one strand that is RNA as long as the INA construct induces enzymatic degradation of a homologous mRNA.

Polar aprotic solvents are solvents that share ion-dissolving power with protic solvents but lack acidic hydrogen. These solvents generally have high dielectric constants and high polarity. Examples of polar aprotic solvents are dimethyl sulfoxide, dimethylformamide, dioxane and hexamethylphosphorotriamide, acetone, acetonitrile, N, N-dimethylformamide (DMF), N-methylpyrrolidone (NMP), dimethylacetamide, dimethyl sulfoxide (DMSO), sulfolane, acetonitrile, hexamethylphosphoric triamide (HMPA), pyridine, tetramethylurea (TMU), urea analogs, N,N-dimethylformamide HCON(CH3)2, N,N-dimethylacetamide (DMA) CH3CON(CH3)2, and tetramethylurea, (CH3)2NCON(CH3)2, 1,3-Dimethyl-2-imidazolidinone (DMI), and 1,3-Dimethyl-3,4,5,6-tetrahydro-2(1H)-pyrimidinone (DMPU). It is possible to substitute the relatively toxic hexamethylphosphoramide (HMPA) with DMPU.

As used herein, the terms "aptamer" or "nucleic acid aptamer" encompass a nucleic acid molecule that binds specifically to a target molecule, wherein the nucleic acid molecule contains a sequence that is recognized by the target molecule in its natural setting. Alternately, an aptamer can be a nucleic acid molecule that binds to a target molecule where the target molecule does not naturally bind to a nucleic acid.

For example, the aptamer can be used to bind to a ligand-binding domain of a protein, thereby preventing interaction of the naturally occurring ligand with the protein. See, for example, Gold, et al., Arum. Rev. Biochem. 64:763, 1995; Brody and Gold, J. Biotechnol. 74:5, 2000; Sun, Curr. Opin. Mol. Then 2:100, 2000; Kusser, J. Biotechnol. 74:27, 2000; Hermann and Patel, Science 287:820, 2000; and Jayasena, Clinical Chemistry 45:1628, 1999.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof. "Antisense RNA" is an RNA strand having a sequence complementary to a target gene mRNA, that can induce RNAi by binding to the target gene mRNA. Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form iNA. These antisense and sense RNAs have been conventionally synthesized with an RNA synthesizer.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

By "RNA" is meant a molecule comprising at least one ribonucleotide residue. By "ribonucleotide" is meant a nucleotide with a hydroxyl group at the 2' position of a βD-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue. A ribonucleotide is a nucleotide with a hydroxyl group at the 2' position of a β-D-ribo-furanose moiety. These terms include double-stranded RNA, single-stranded RNA, isolated RNA such as partially purified RNA, essentially pure RNA, synthetic RNA, recombinantly produced RNA, as well as modified and altered RNA that differs from naturally occurring RNA by the addition, deletion, substitution, modification, and/or alteration of one or more nucleotides. Alterations of an RNA can include addition of non-nucleotide material, such as to the end(s) of an interfering RNA or internally, for example at one or more nucleotides of an RNA nucleotides in an RNA molecule include non-standard nucleotides, such as non-naturally occurring nucleotides or chemically synthesized nucleotides or deoxynucleotides. These altered RNAs can be referred to as analogs.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein complementary nucleotide bases are a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (join by hydrogen bonding) with each other. By "complementarity" is meant that a nucleic acid can form hydrogen bond(s) with another nucleic acid sequence either by traditional Watson-Crick or by other non-traditional modes of binding.

Antagomirs are one of a novel class of chemically engineered antisense oligonucleotides. Antagomirs are used in the silencing of endogenous microRNA.

MicroRNAs (miRNA) are single-stranded RNA molecules of about 21-23 nucleotides in length, which regulate gene expression miRNAs are encoded by genes that are transcribed from DNA but not translated into protein (non-doding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression As used herein the term small interfering RNA (siRNA), sometimes known as short interfering RNA or silencing RNA, is used to refer to a class of double-stranded RNA molecules, 16-29 nucleotides in length, that play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome; the complexity of these pathways is only now being elucidated.

As used herein, the term RNAi refers to an RNA-dependent gene silencing process that is controlled by the RNA-induced silencing complex (RISC) and is initiated by short double-stranded RNA molecules in a cell, where they interact with the catalytic RISC component argonaute. When the double-stranded RNA or RNA-like iNA or siRNA is exogenous (coming from infection by a virus with an RNA genome or from transfected iNA or siRNA), the RNA or iNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex. The active components of an RNA-induced silencing complex (RISC) are endonucleases called argonaute proteins, which cleave the target mRNA strand complementary to their bound siRNA or iNA. As the fragments produced by dicer are double-stranded, they could each in theory produce a functional siRNA or iNA. However, only one of the two strands, which is known as the guide strand, binds the argonaute protein and directs gene silencing. The other anti-guide strand or passenger strand is degraded during RISC activation.

Examples of preservatives include phenol, methyl paraben, paraben, m-cresol, thiomersal, benzylalkonium chloride, and mixtures thereof.

Core Complex

The formulation is preferably formed by putting the cationic lipid nucleic acid salt in solution in an organic solvent, in particular in an aprotic polar solvent and mixed with a solution of one or more lipids mentioned above. The lipids are in solution in an organic solvent, preferably an aprotic polar solvent.

Examples of cationic lipids that can be used in creating the cationic lipid nucleic acid salts include any of a number of lipid species that carry a net positive charge at a selected pH, such as physiological pH (e.g., pH of about 7.0). As used herein, physiological pH refers to the pH of a biological fluid such as blood or lymph as well as the pH of a cellular compartment such as an endosome, an acidic endosome, or a lysosome). Such lipids include, but are not limited to, N,N-dioleyl-N,N-dimethylammonium chloride ("DODAC"); N-(1-(2,3-dioleyloxy)propyl)-N,N,N-trimethylammonium chloride ("DOTMA); N,N-dimethyl-(2,3-dioleyloxy)propylamine ("DODMA"); N,N-distearyl-N,N-dimethylammonium bromide ("DDAB"); N-(1-(2,3-dioleoyloxy)propyl)-N,N,N-trimethylammonium chloride ("DOTAP"); 3-(N—(N', N'-dimethylaminoethane)-carbarnoyl)cholesterol ("DC-Chol"); N-(1,2-dimyristyloxyprop-3-yl)-N,N-dimethyl-N-hydroxyethyl ammonium bromide ("DMRIE"); 1,2-Dilinoleyloxy-N,N-dimethylaminopropane (DLinDMA); and 1,2-Dilinolenyloxy-N,N-dimethylaminopropane (DLenDMA). The following lipids are cationic and have a positive charge at below physiological pH: 1,2-dimyristoyl-3-dimethylammonium propane (DODAP), DODMA, DMDMA and the like. These lipids and related analogs have been described in copending U.S. Ser. No. 08/316,399; U.S. Pat. Nos. 5,208,036, 5,264,618, 5,279,833 and 5,283,185. Additionally, a number of commercial preparations of cationic lipids are available and can be used in the present disclosure.

The cationic organic salt precipitate of nucleic acid of certain organic cations of carbon number greater than 6, preferably greater than 15, most preferably greater than 18, can be readily solvated in many common organic solvents including solvents that are of the polar aprotic class (dimethylacetamide, dimethylformamide, N-methyl pyrrolidine, diglyme and other ether glycols, chloroform, methylene chloride and other halogenated organic solvents, tetrahydrofiran and other cyclic ether solvents). These solvents can be employed under anhydrous conditions and are of industrial value for the use in chemical transformation and reaction of reagents into new chemical forms.

Contacting the nucleic acid solution with the solution of cationic lipids is accomplished by mixing together a solution of nucleic acids, which is typically an aqueous solution, with a solution of the cationic lipids. The cationic lipid can be in solution in either an organic or aqueous solvent. The ratio of cationic lipid to nucleotides present in nucleic should be preferably 2-3 to 1 by weight. One of skill in the art will understand that this mixing can take place by any number of methods, for example by mechanical means such as by using vortex, mixers or injection pumps and stirred reactors.

Formulations with Colipids

In as much as compounds designed to facilitate intracellular delivery of biologically active molecules especially nucleic acid molecules, such as DNA and siRNA are mostly with polar and non-polar domains which can interact with both polar and non-polar environments. Compounds having both such domains may be termed amphiphiles, and many lipids and synthetic lipids that have been disclosed for use in facilitating such intracellular delivery (whether for in vitro or in vivo application) meet this definition.

The core complex may be combined with colipids in an organic or polar aprotic solvent. The colipids are one or more lipids selected from the group consisting of (i) lipid carbamates, (ii) neutral phospholipids, (iii) sterols, and (iv) sterol-PEG compounds.

Lipid carbamates include the following molecules:

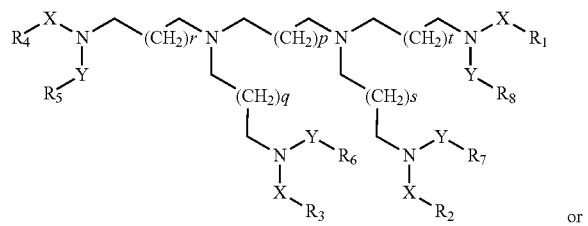

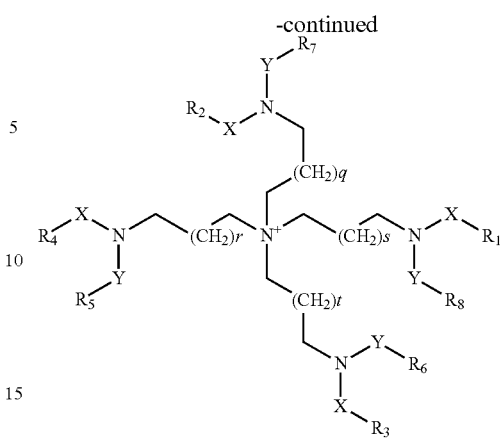

wherein p, q, r, s and t; are each independently chosen from 0 to 16;
X and Y are each independently chosen from the group consisting of H, Ac, Boc, or Piv, or from a linker group consisting of C, amide, carbamate, succinamide, maleimide, epoxide, and urethane; and
$R_1$, $R_2$, $R_3$, $R_4$, $R_5$, $R_6$, $R_7$, and $R_8$ are each independently chosen from a group consisting of a C1-C26 alkane or alkene, a polyunsaturated lipid, a steroid, a PUFA, guanidine or arginine, in any combination; and wherein the steroid is selected from the group consisting of lanosterol, ergosterol, desmosterol, a plant phytosterol, such as stigmasterol, or a bile salt or bile salt derivative such as cholic acid, deoxycholic acid, hydrodeoxycholic acid or dehydrocholic acid.

Preferred embodiments are provided in the following list (Groups α, β, and γ; Formulas I-LXVIII), wherein $R_1$ is H; $R_2$ is Me or tert-butoxycarbonyl (Boc); $R_1$, and $R_2$ are guanidinyl or N—CNNH); or $R_1$ is H and $R_2$ is arginine via an amide bond formation. The cholesterol moiety may be replaced by lanosterol, ergosterol, desmosterol, a plant phytosterol such as stigmasterol, or a bile salt or bile salt derivative such as cholic acid, deoxycholic acid, hyodeoxycholic acid and dehydrocholic acid.

Group α lipids:

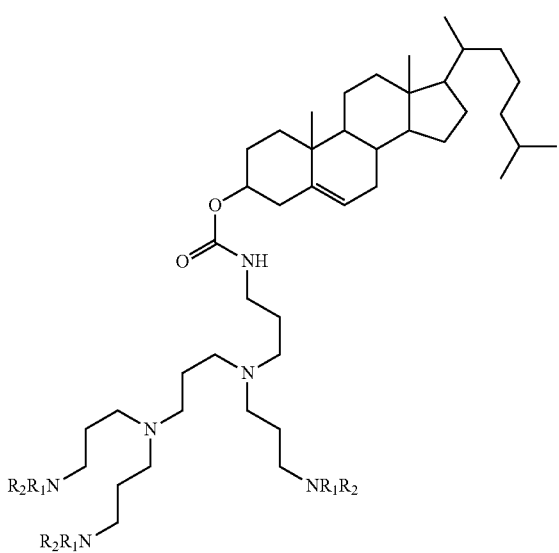

I

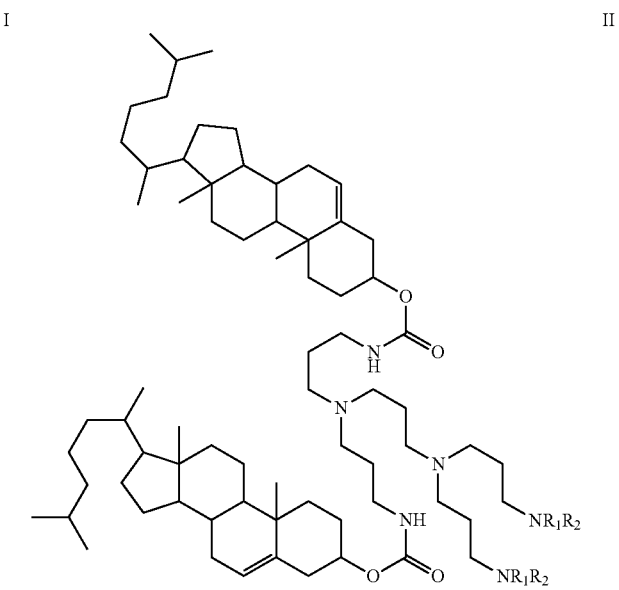

II

-continued
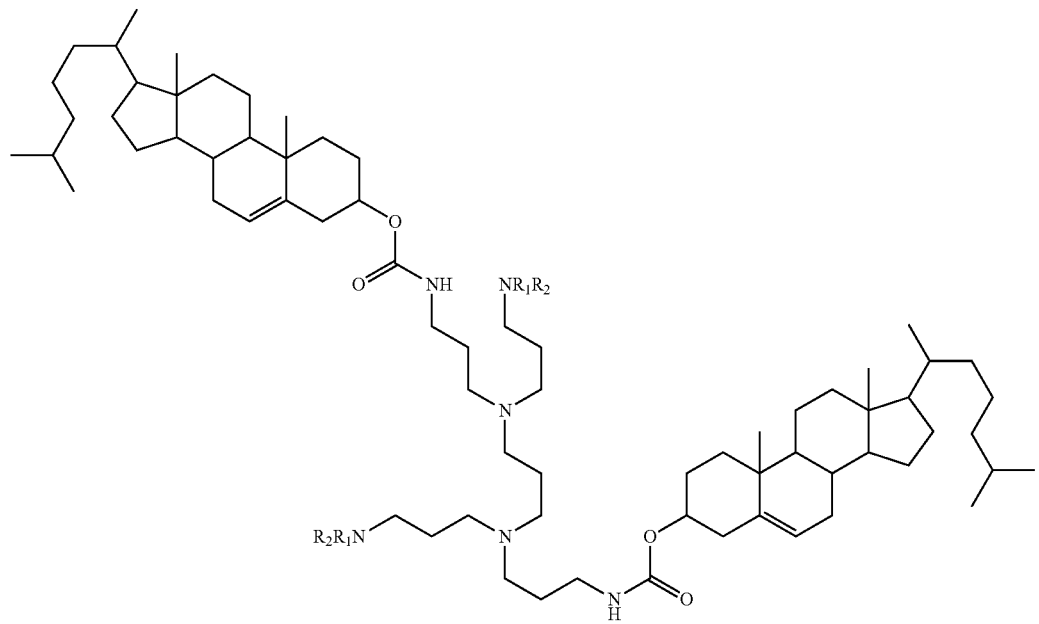
III
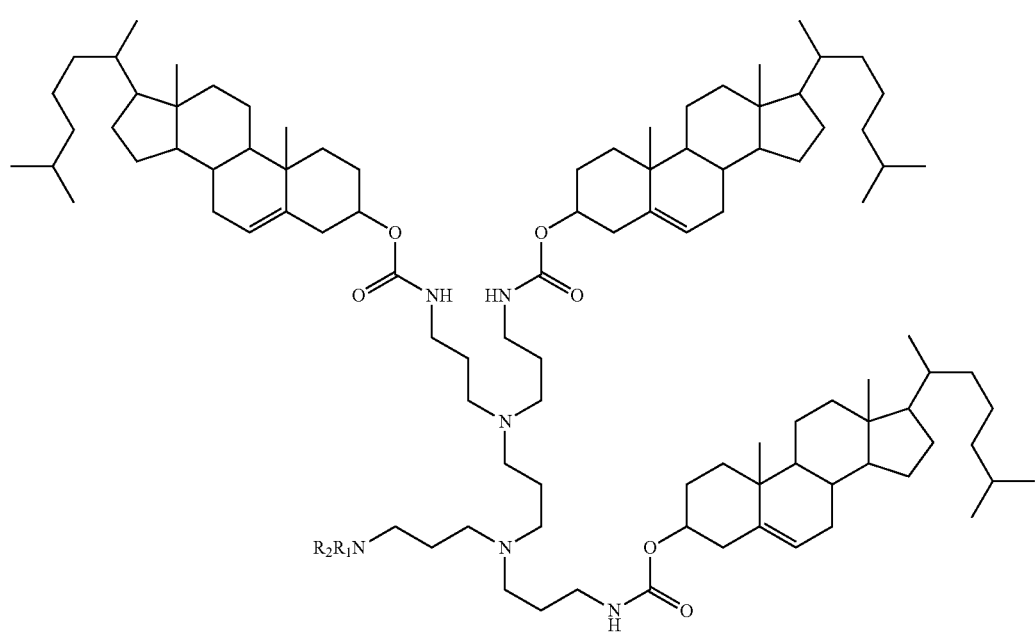
IV

-continued
V
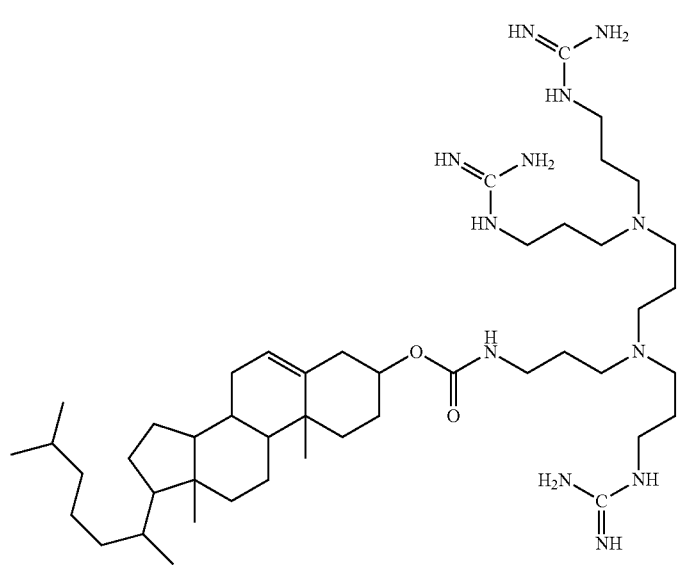
VI
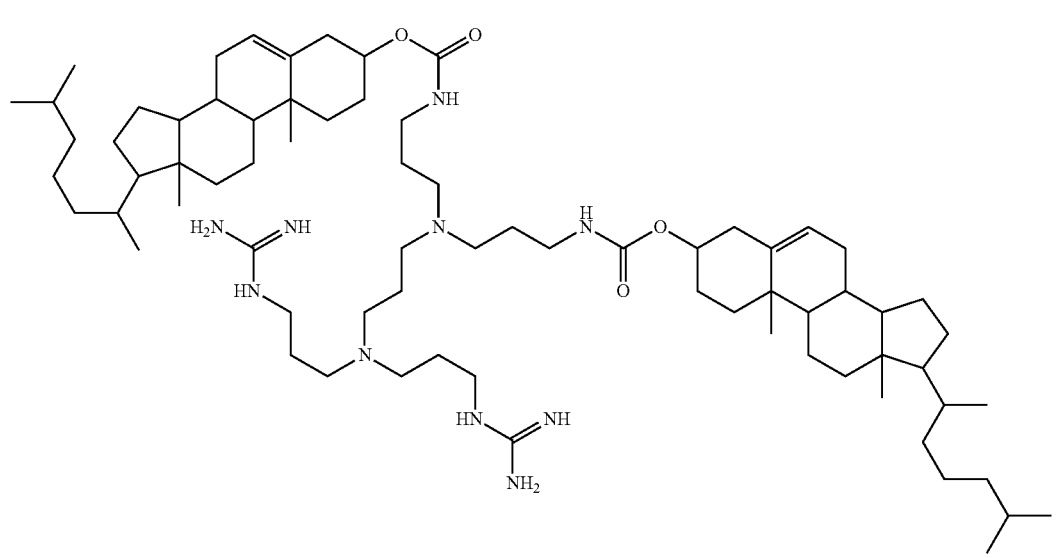
2-regio-isomers of the same Di-Chol derivative
VII
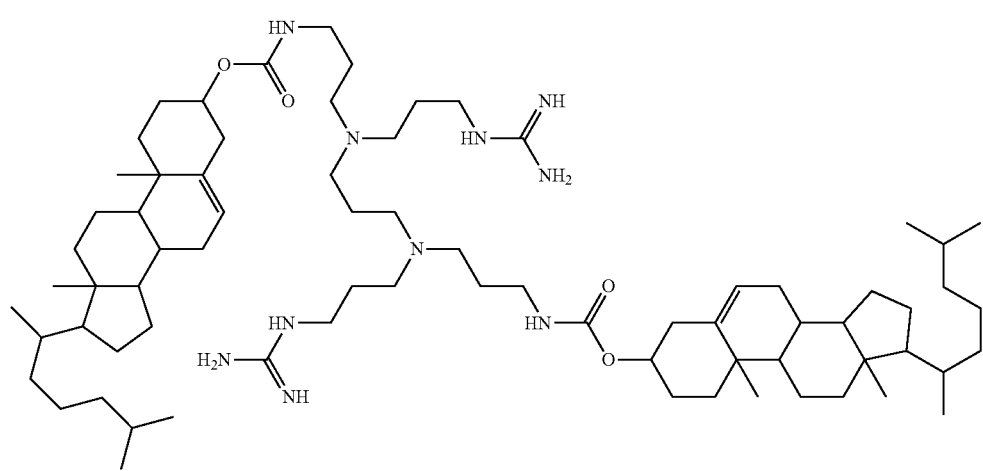

-continued
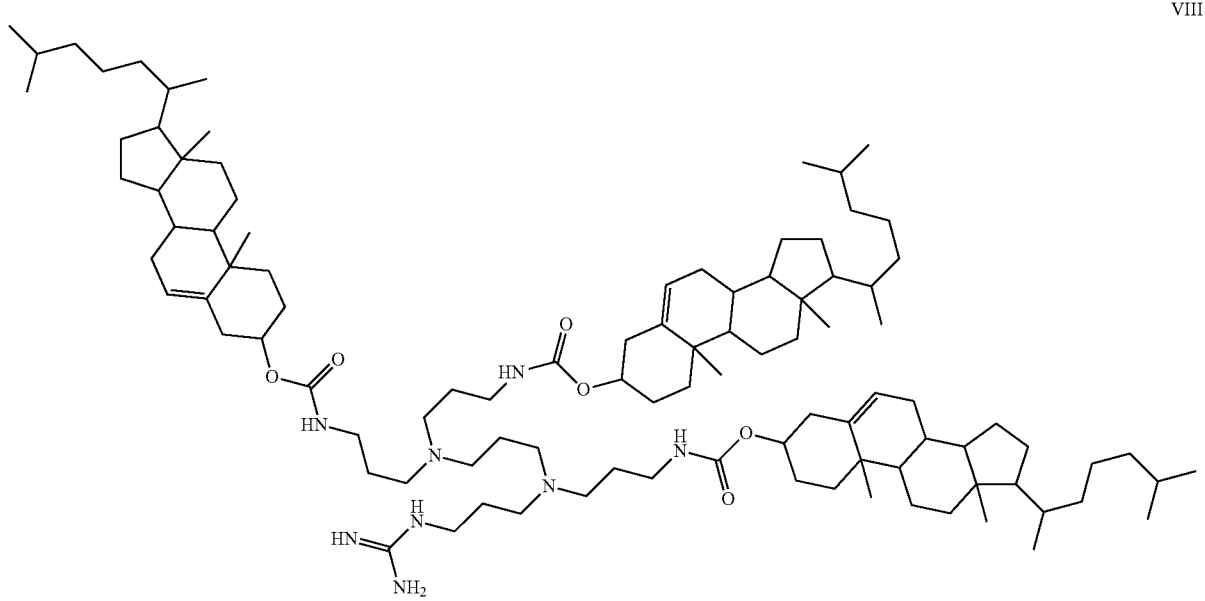
VIII
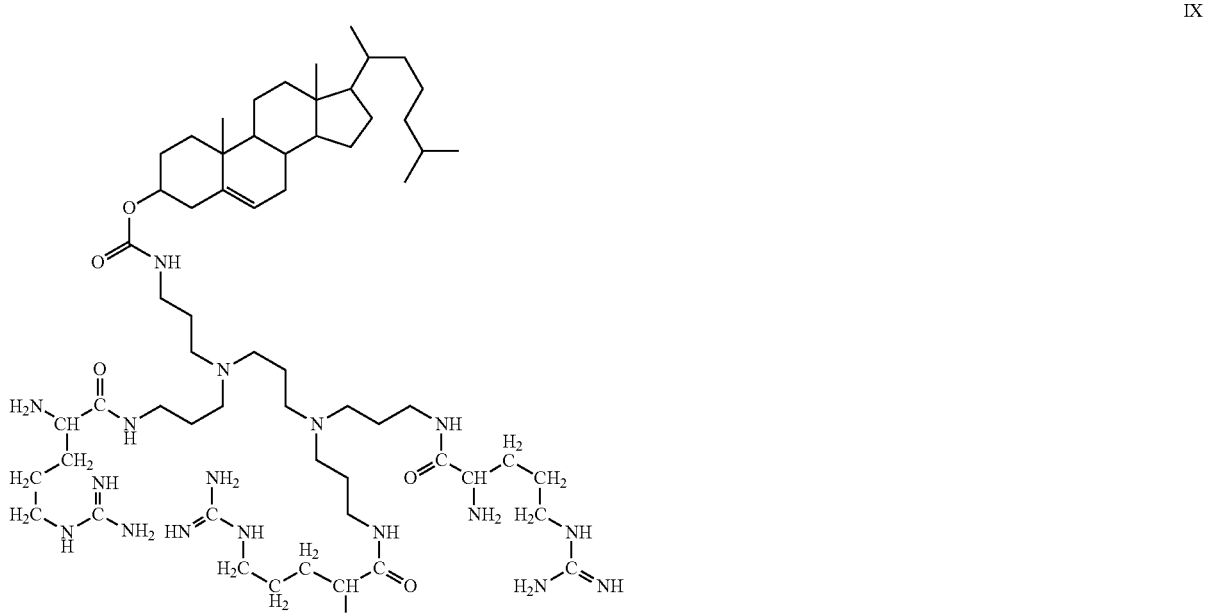
IX
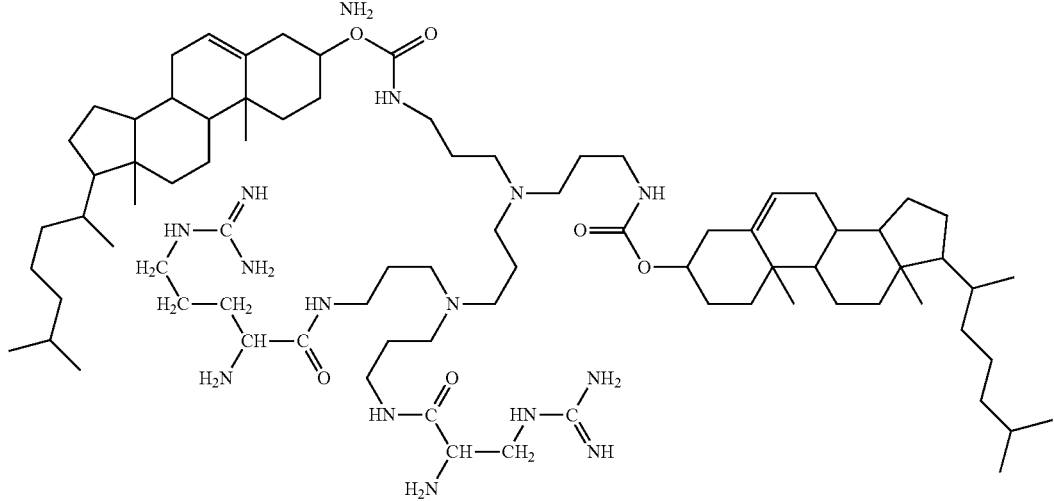
X

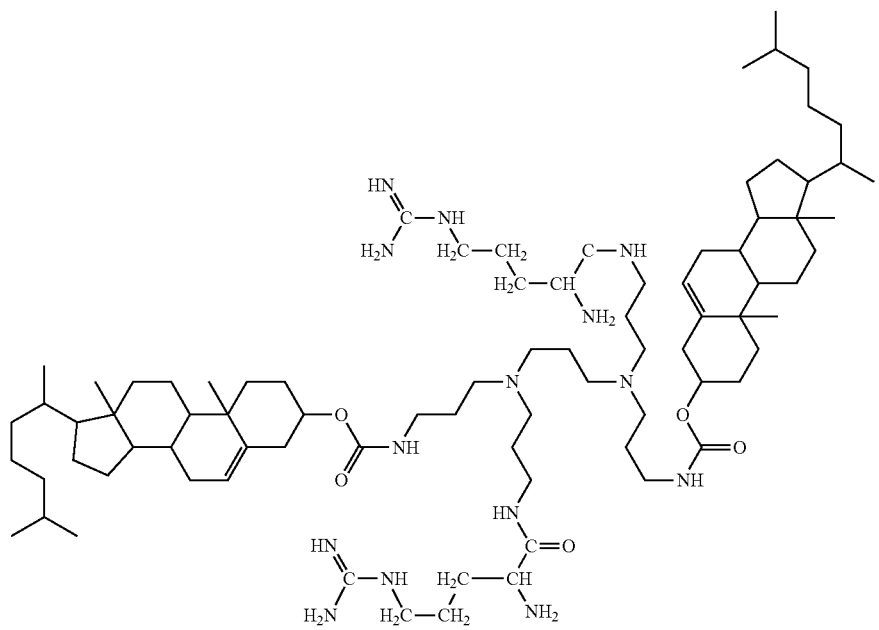
XI
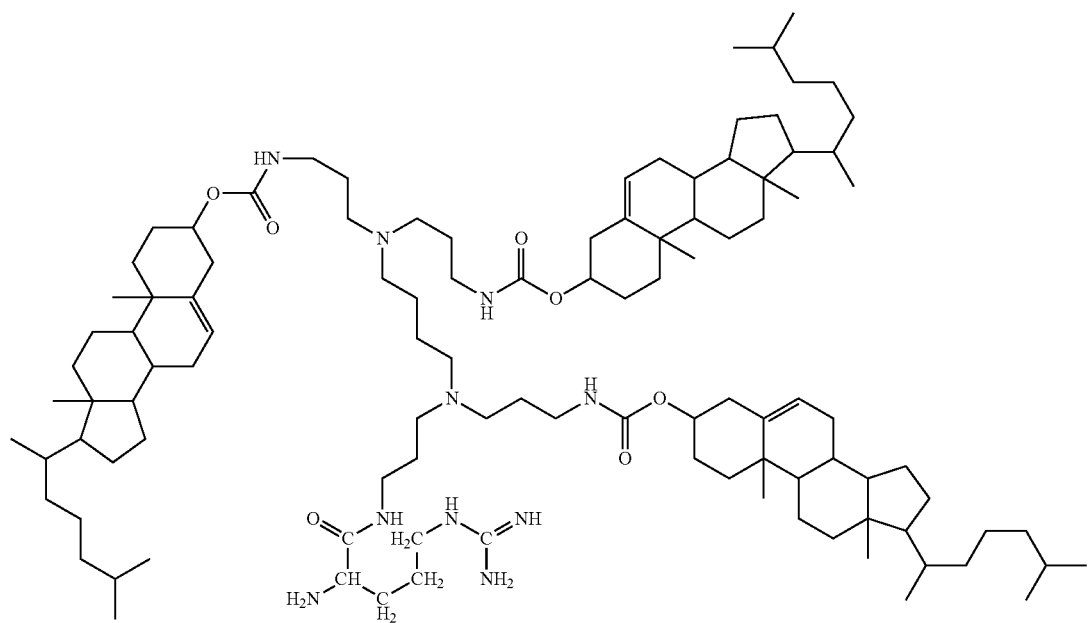
XII
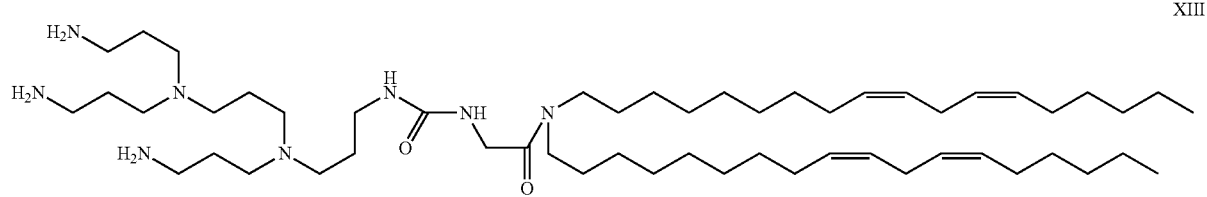
XIII

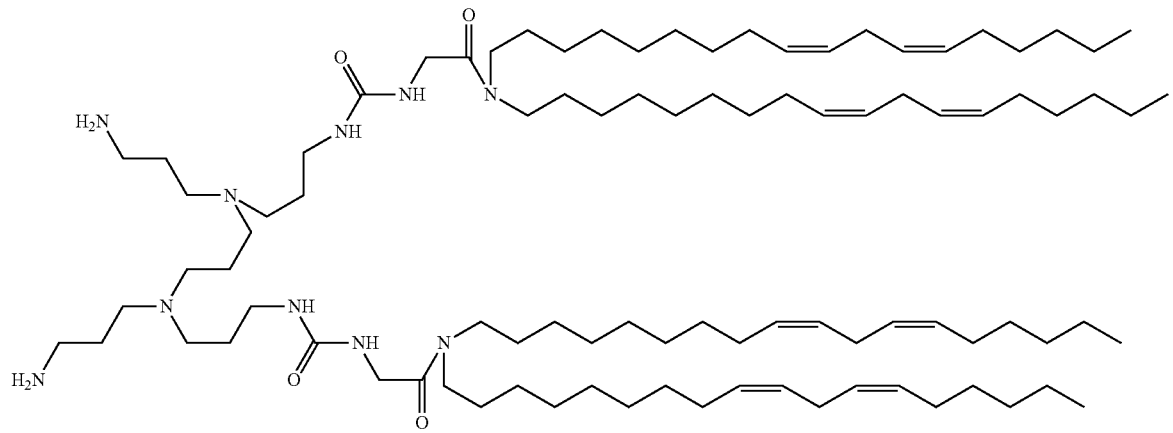
XIV
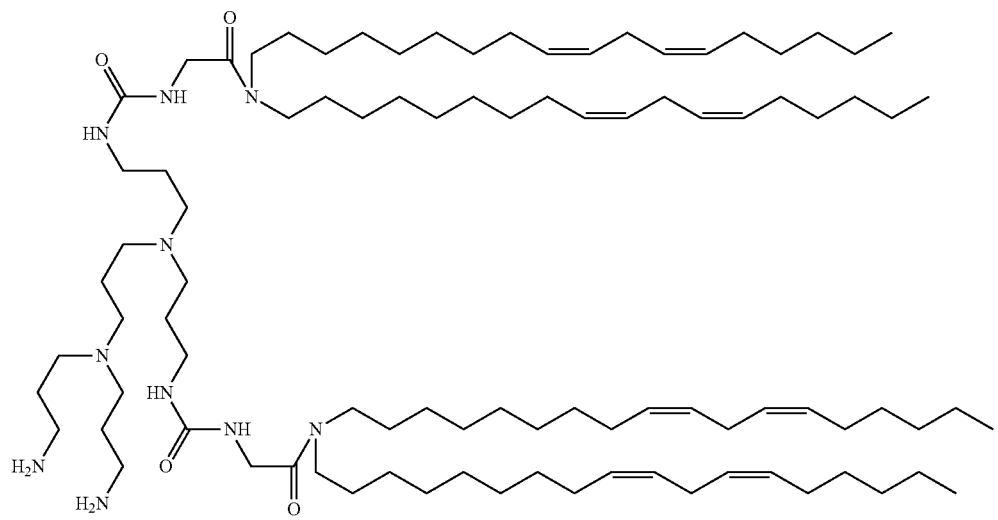
XV
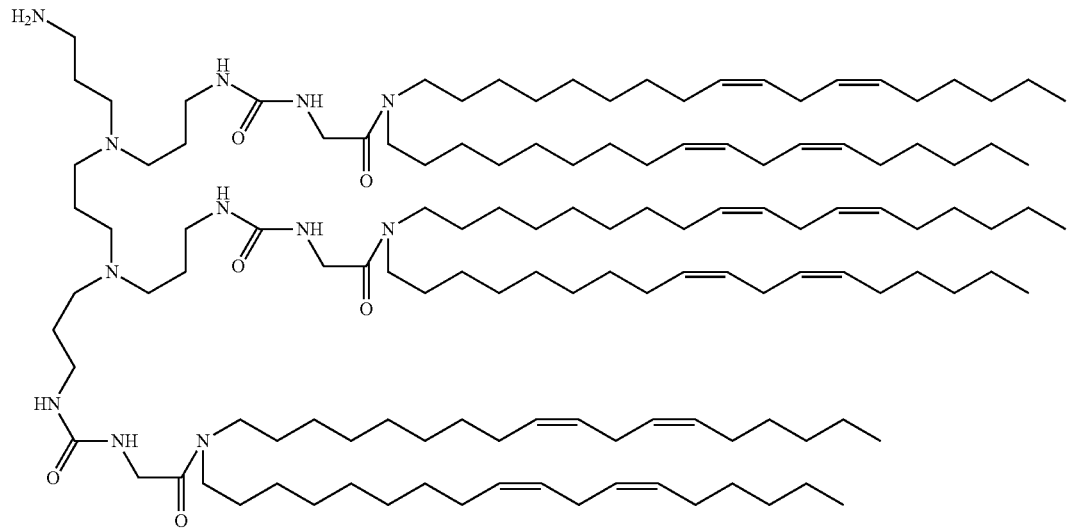
XVI

Group β lipids
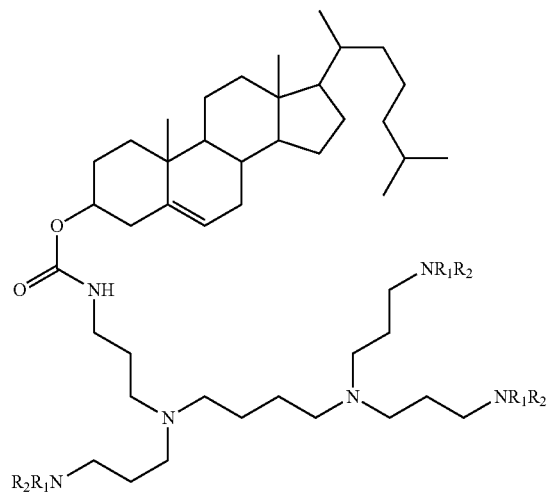
XVII
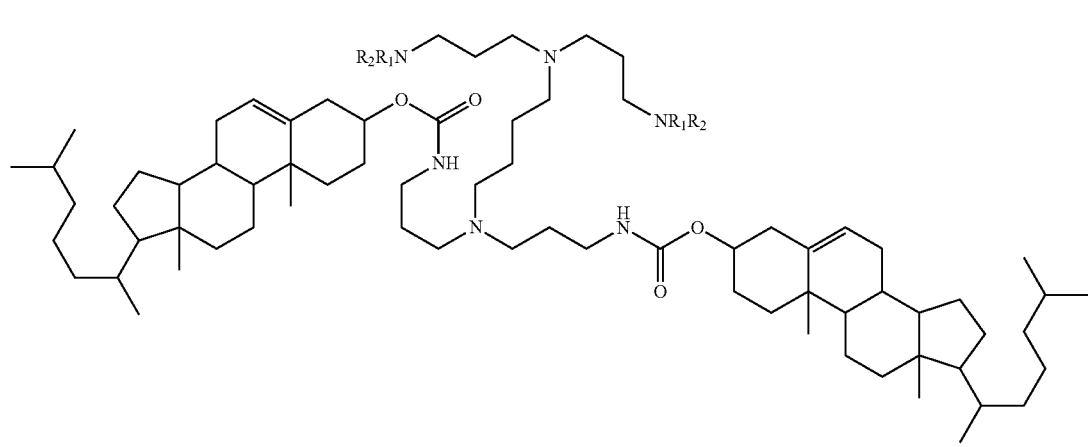
XVIII
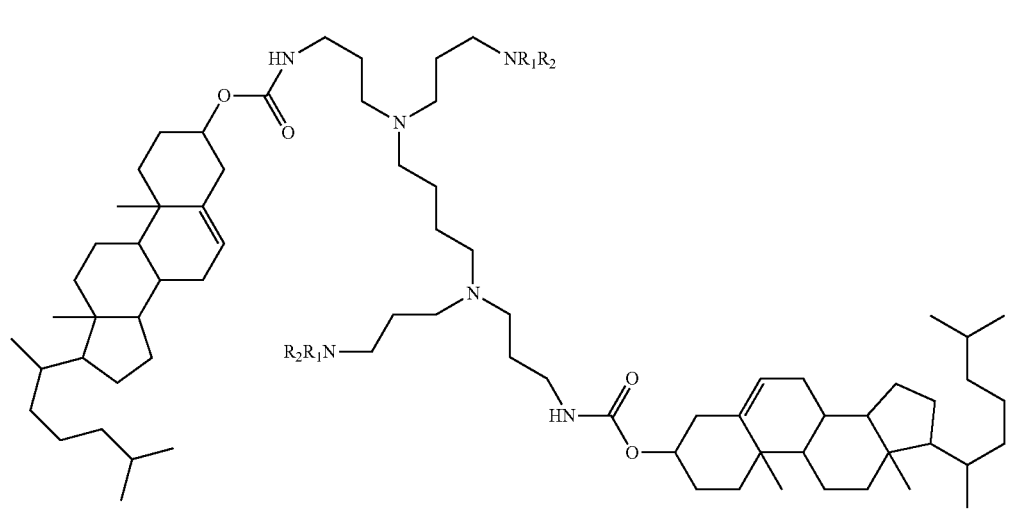
XIX

-continued
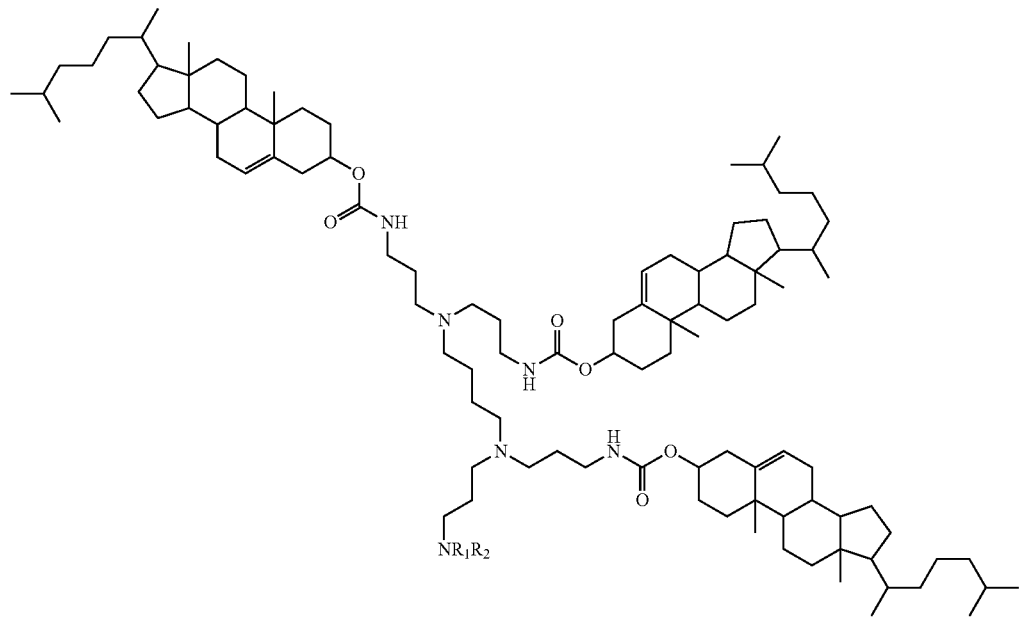
XX
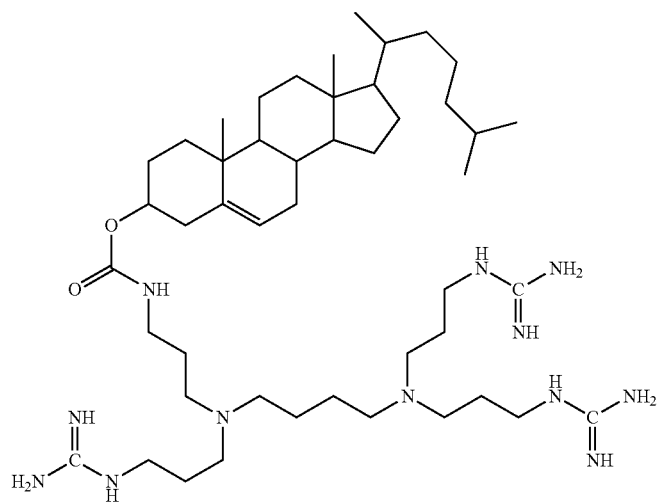
XXI
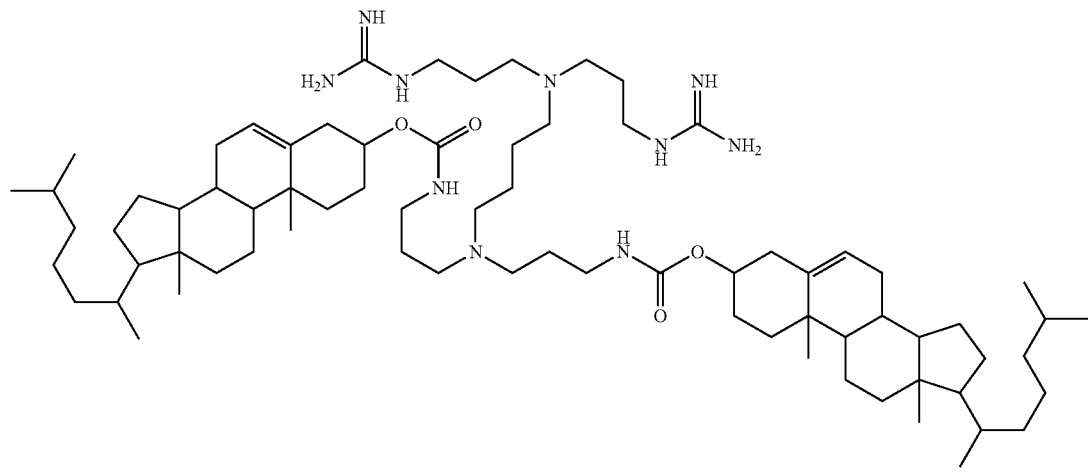
XXII

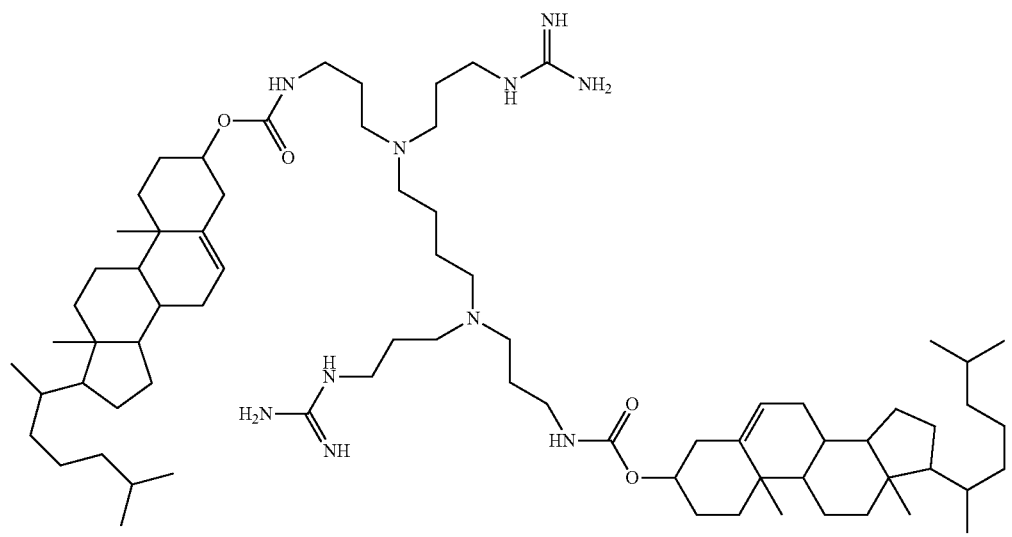
XXIII
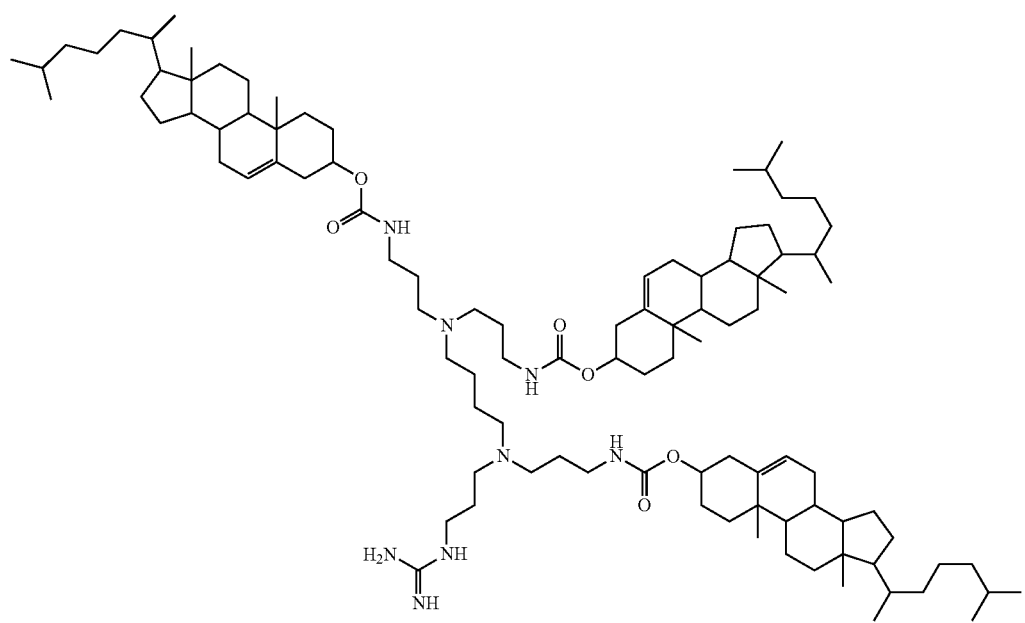
XXIV

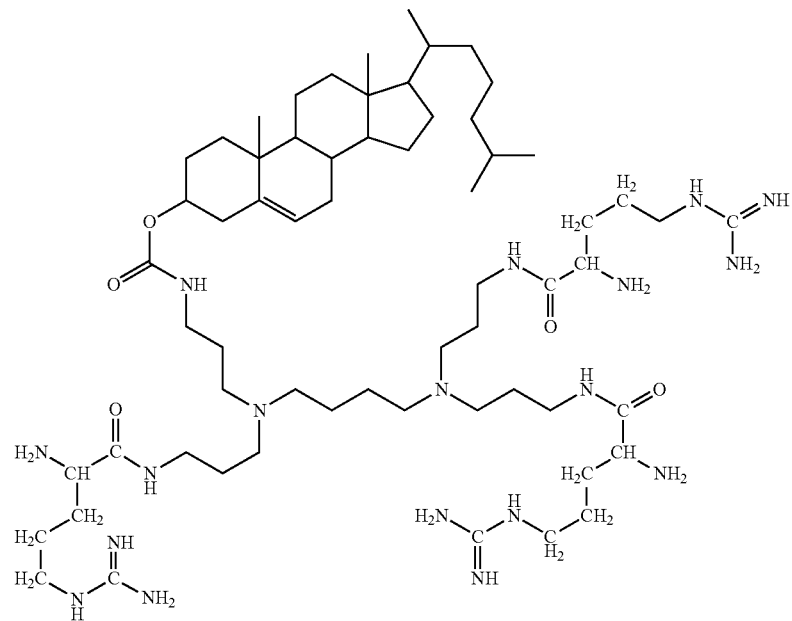
XXV
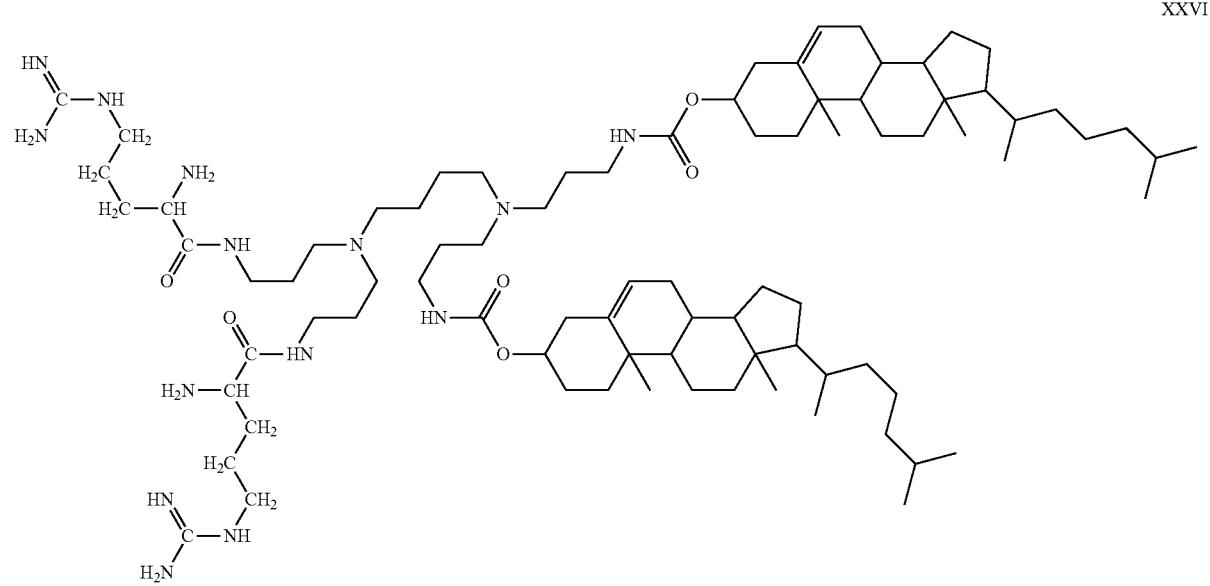
XXVI

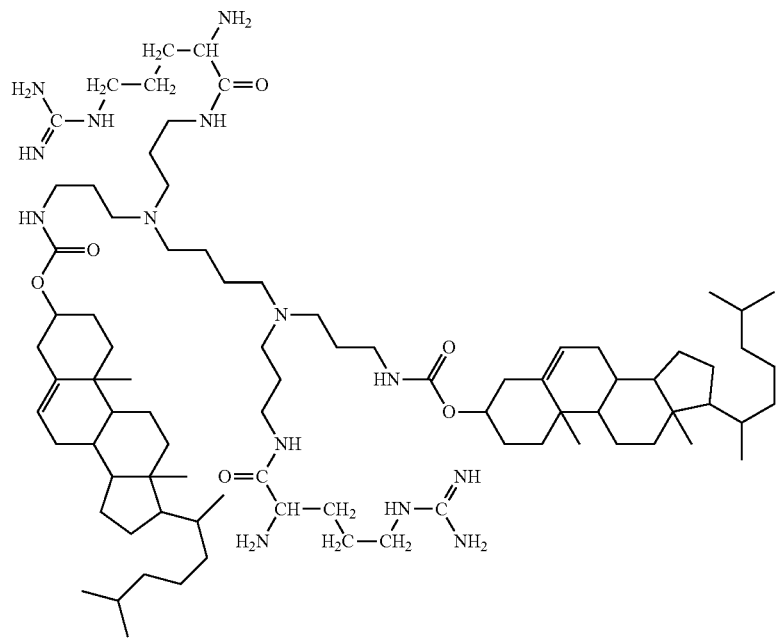
XXVII
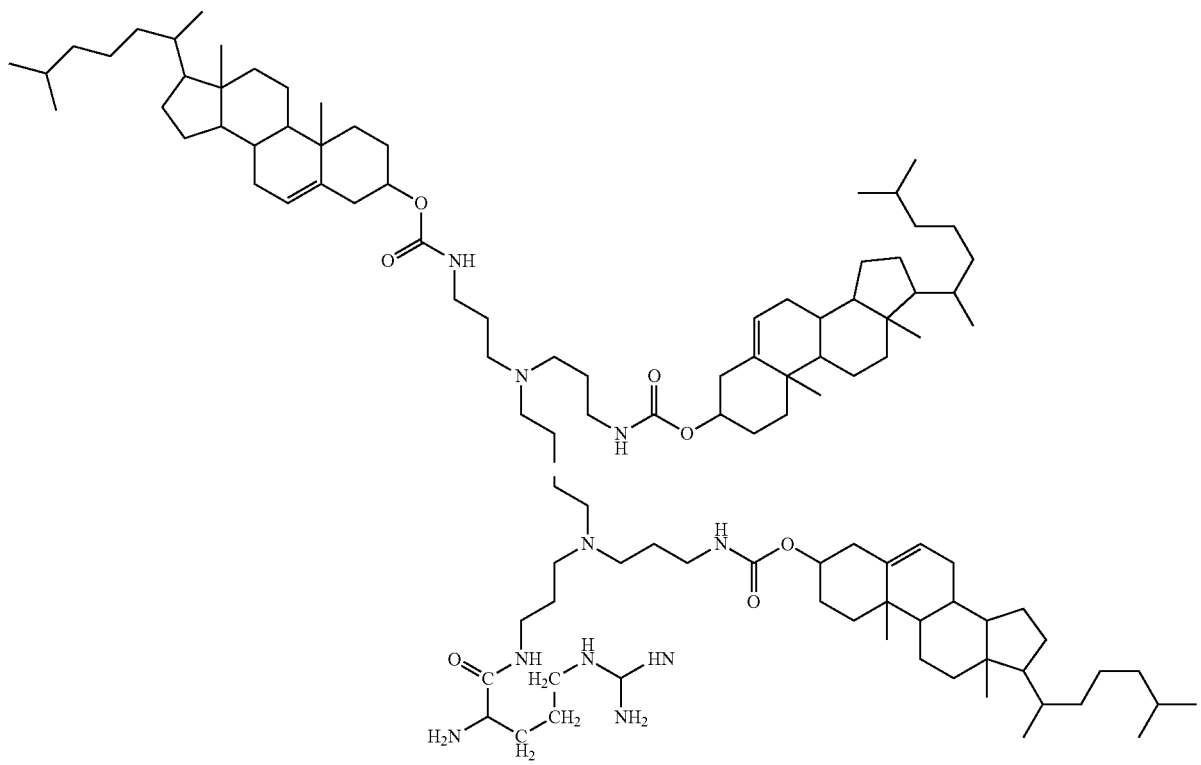
XXVIII
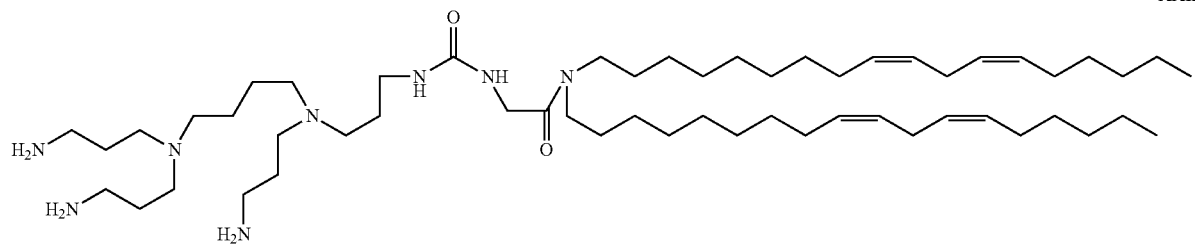
XXIX

-continued
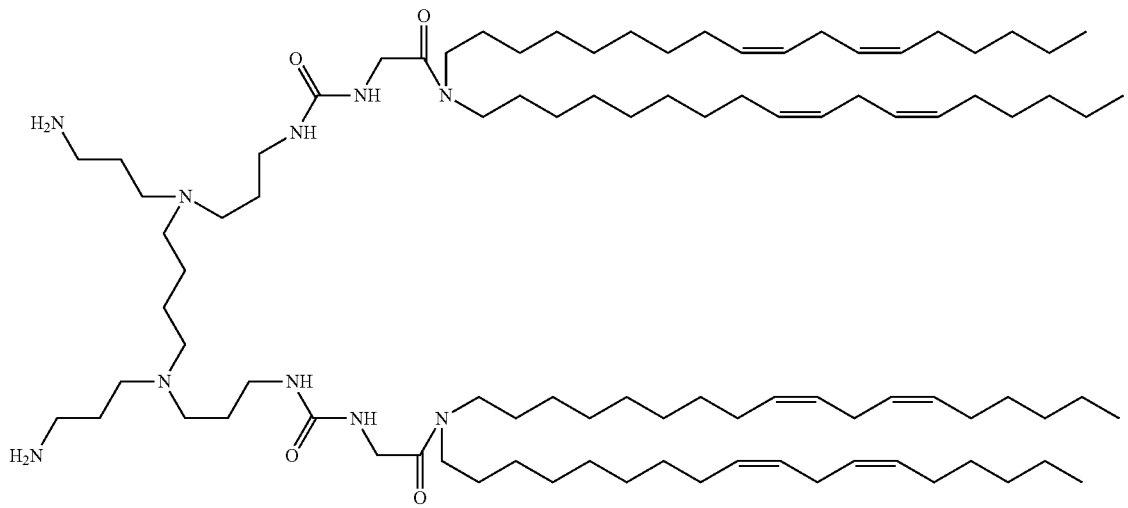
XXX
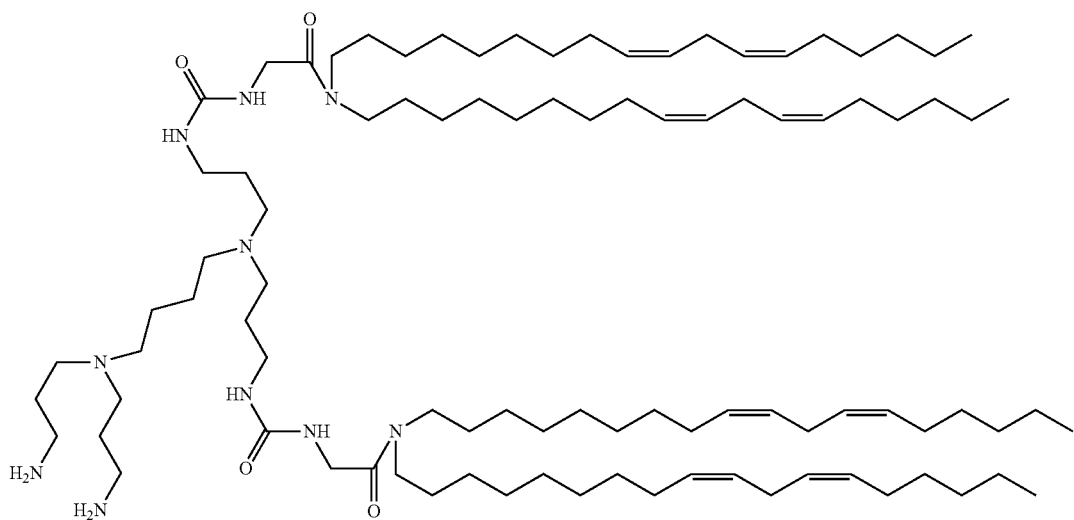
XXXI
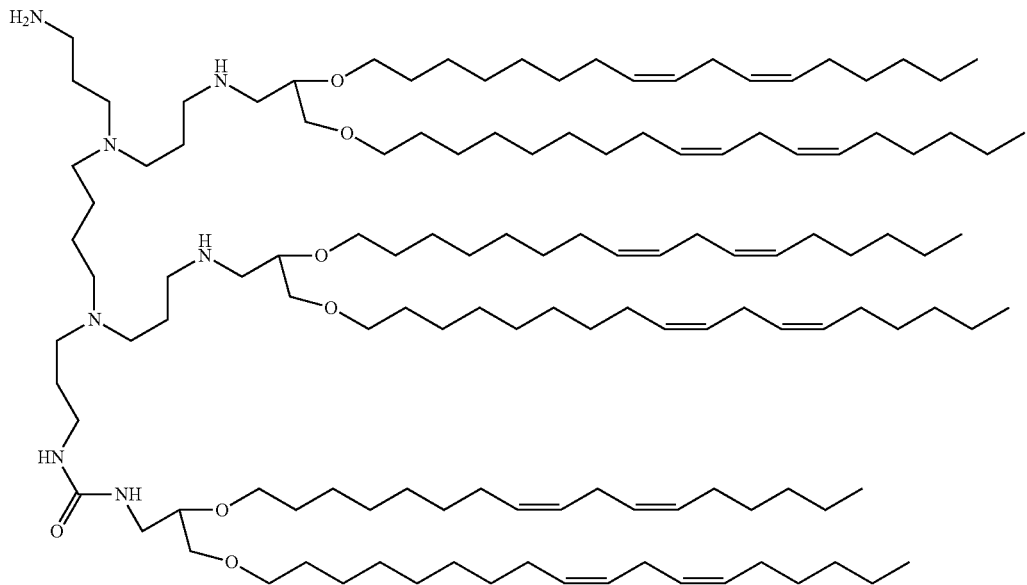
XXXII

Group γ lipids
XXXIII
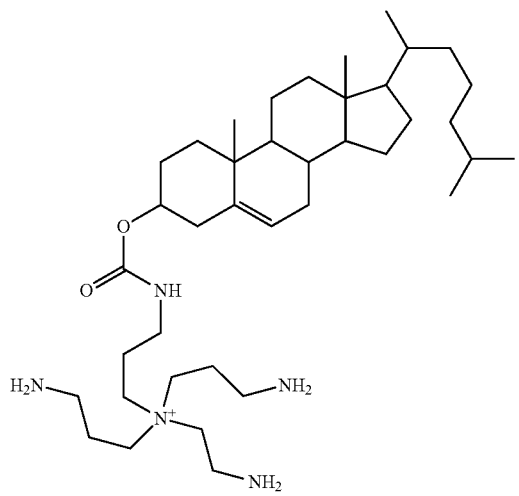
XXXIV
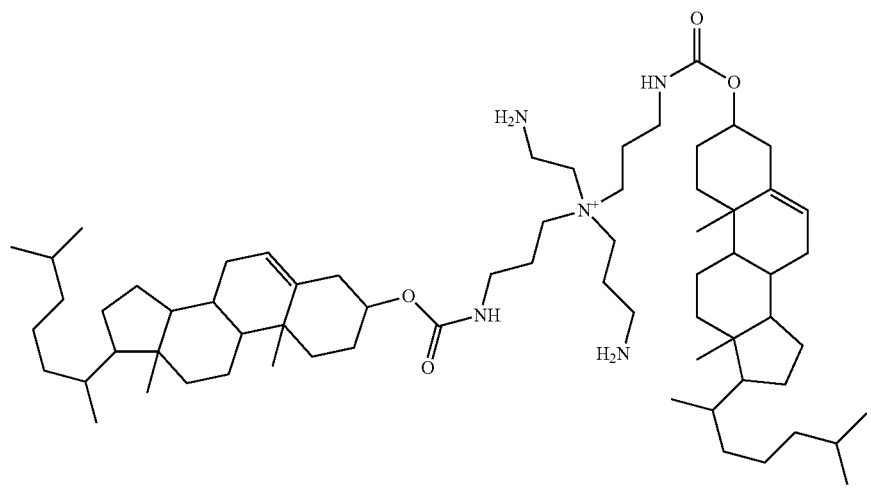
XXXV
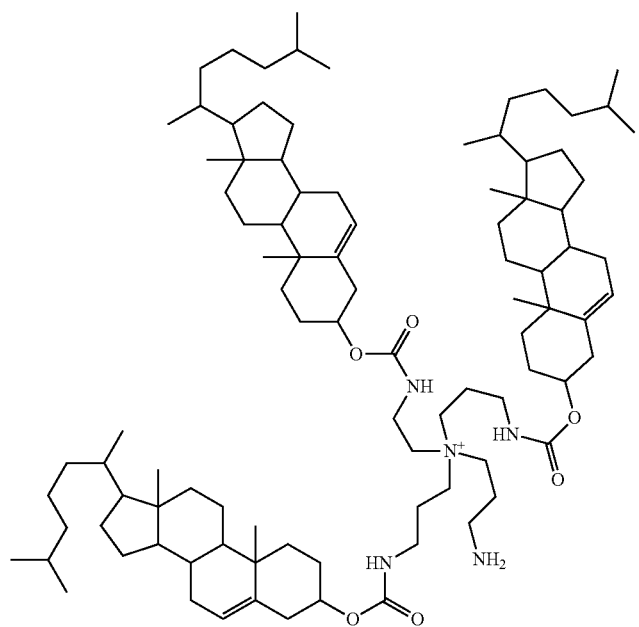

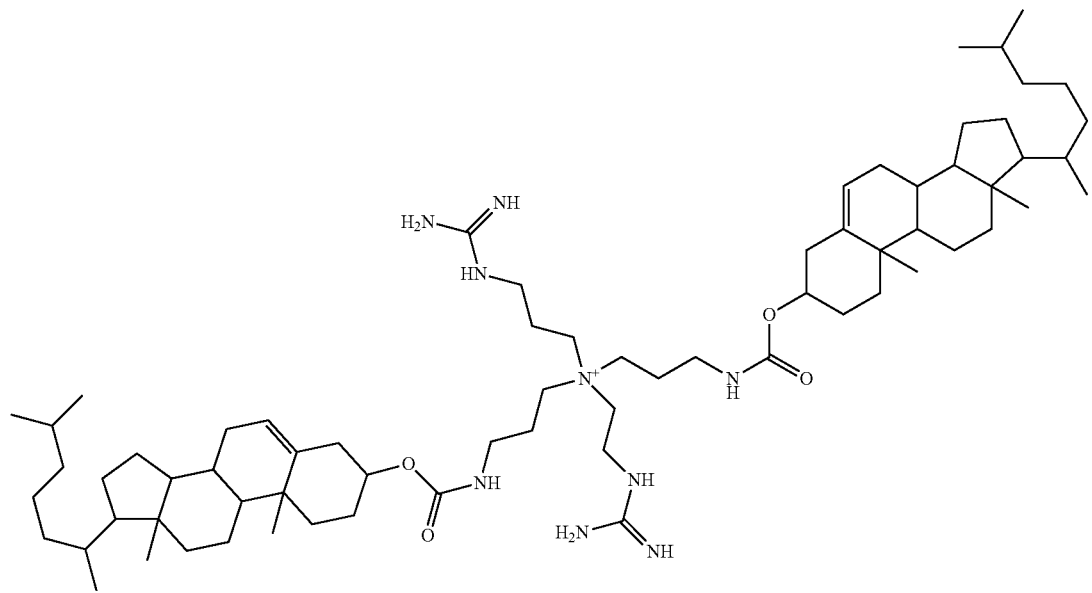
XXXVI
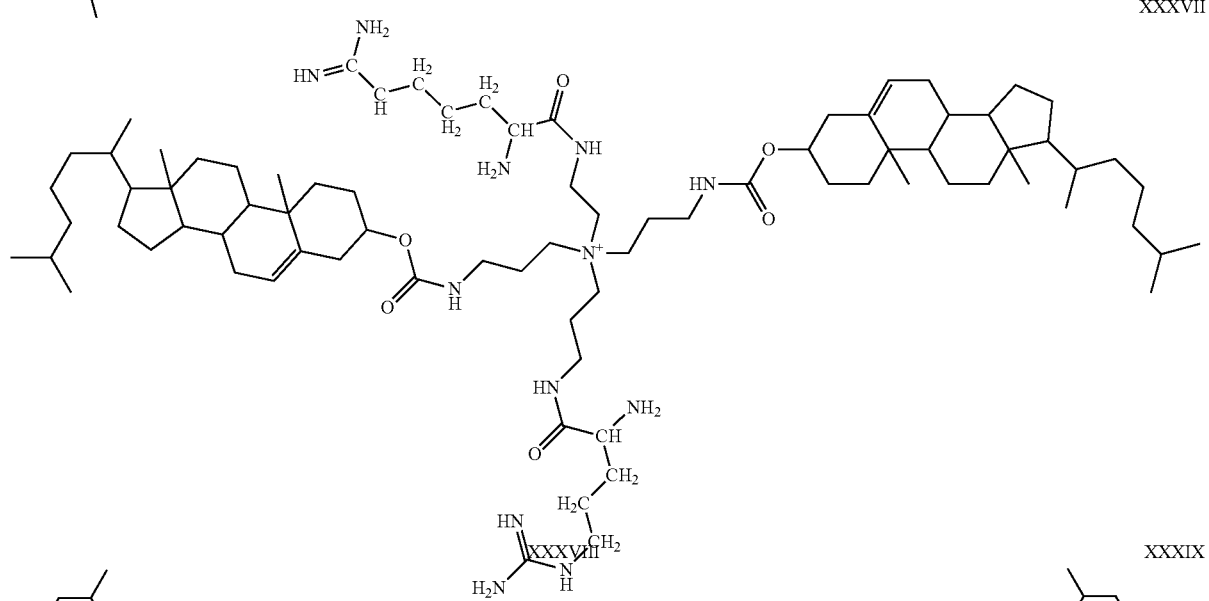
XXXVII
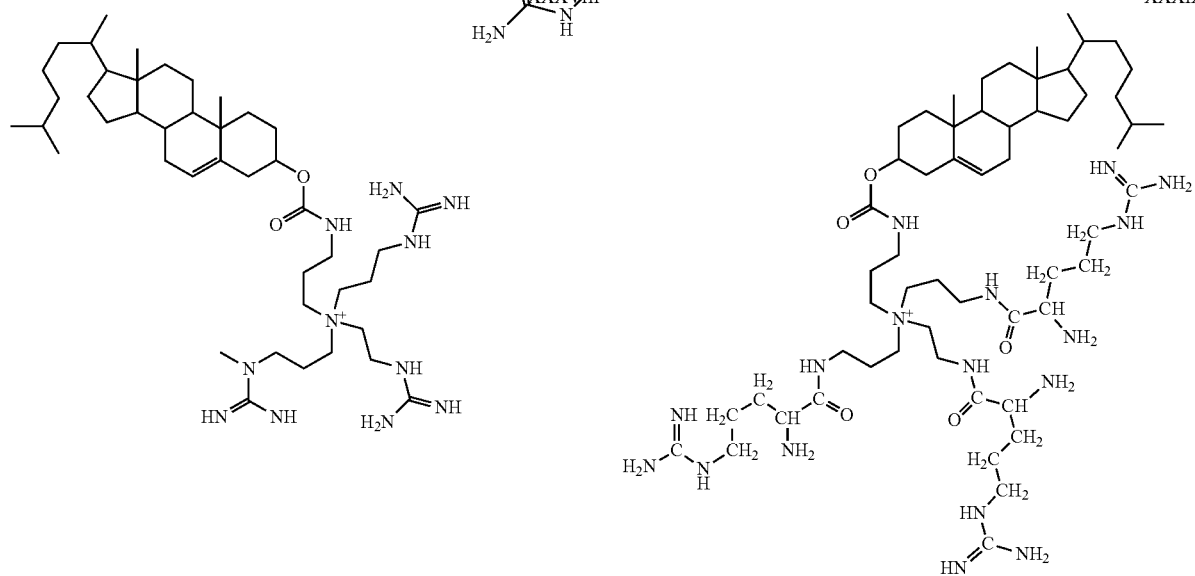
XXXVIII
XXXIX

-continued
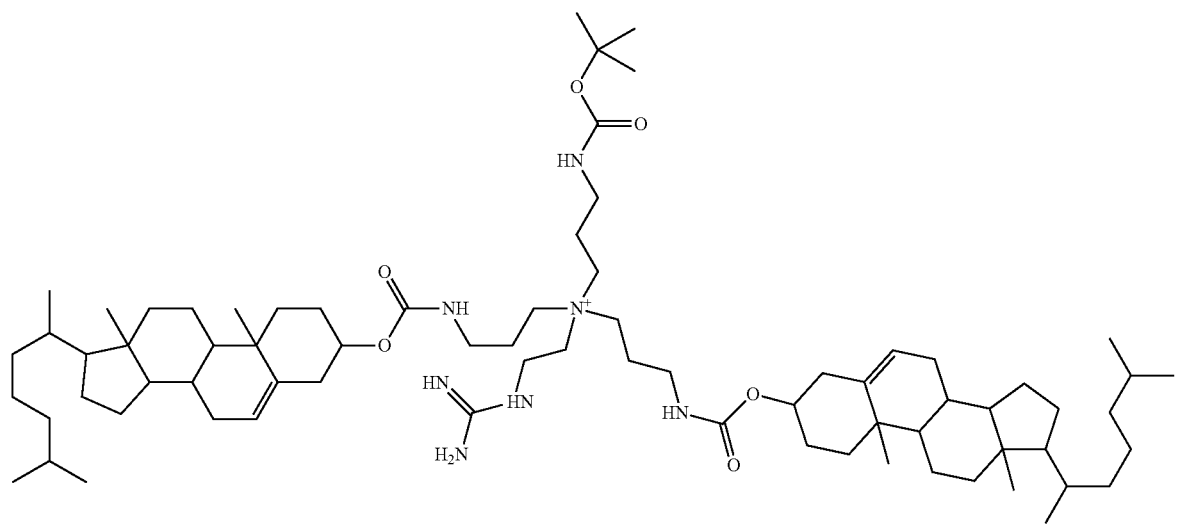
XL
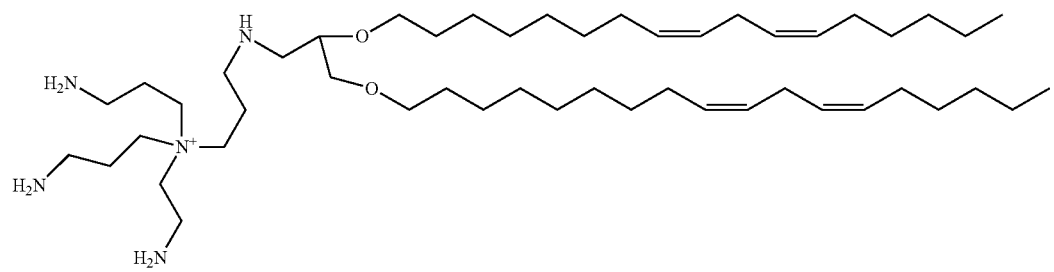
XLI
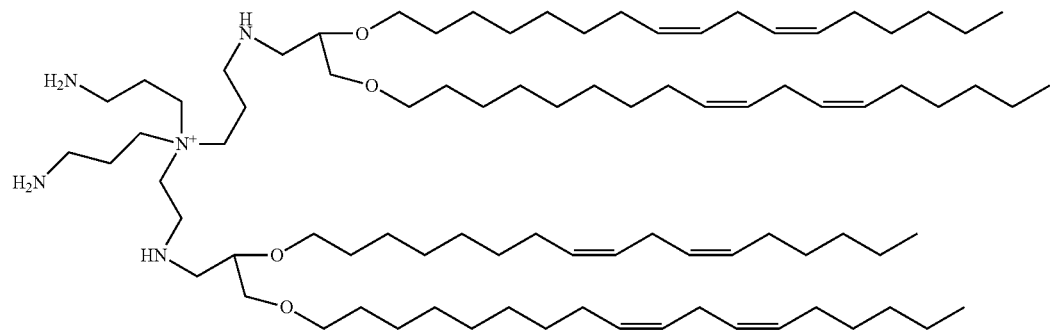
XLII
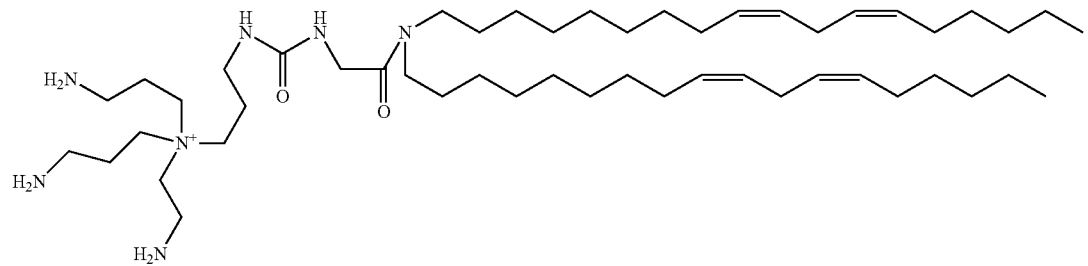
XLIII

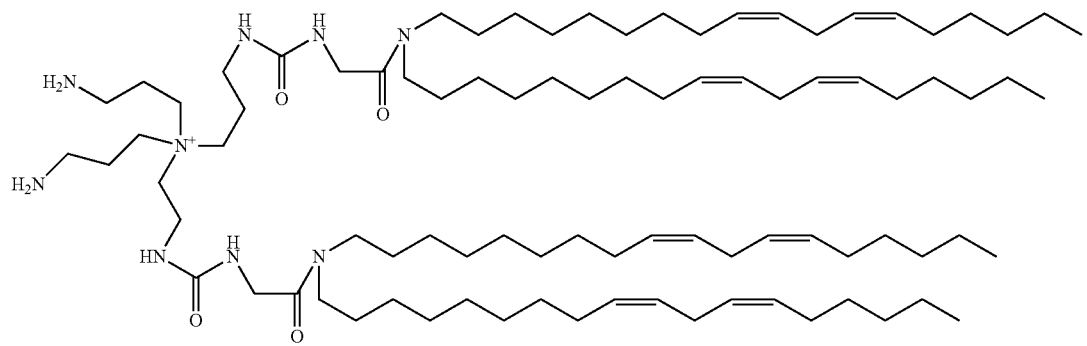
XLIV
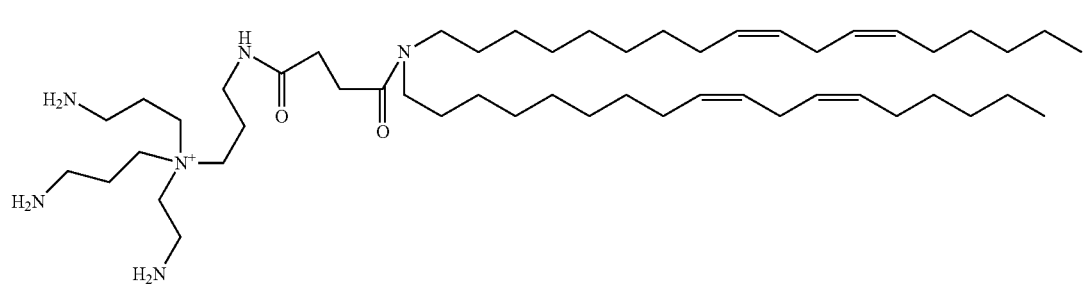
XLV
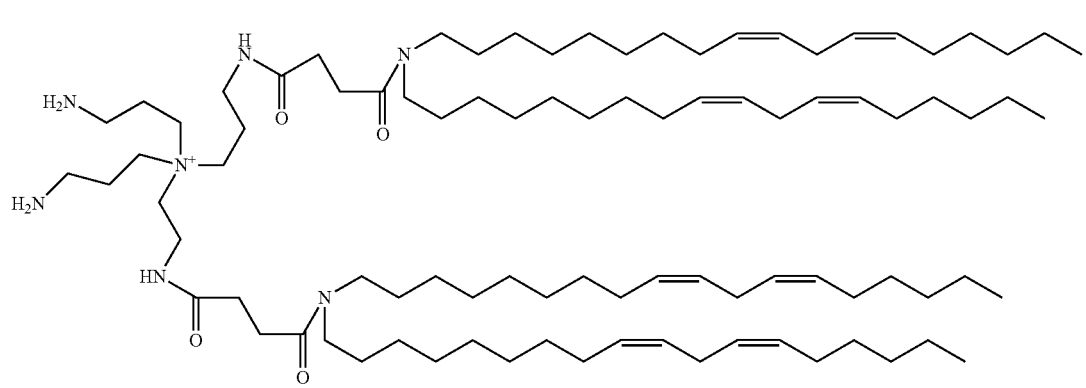
XLVI
Other examples of molecules derived from three basic polyamine molecules are as follows:
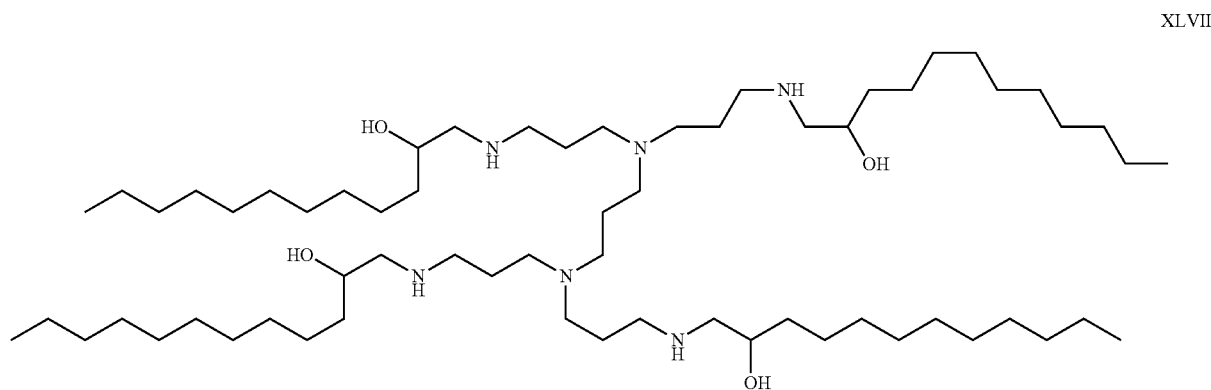
XLVII

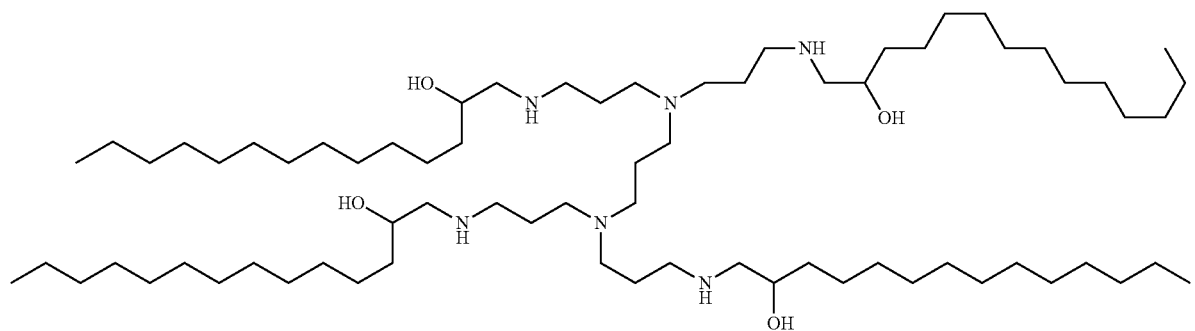
XLVIII
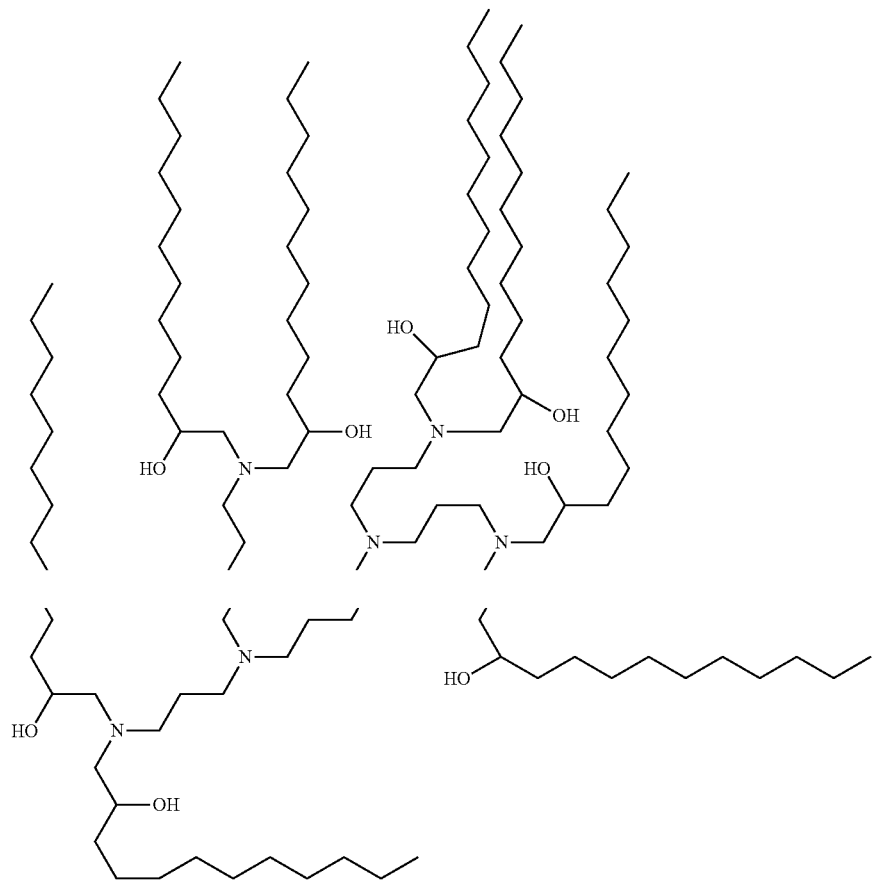
XLIX
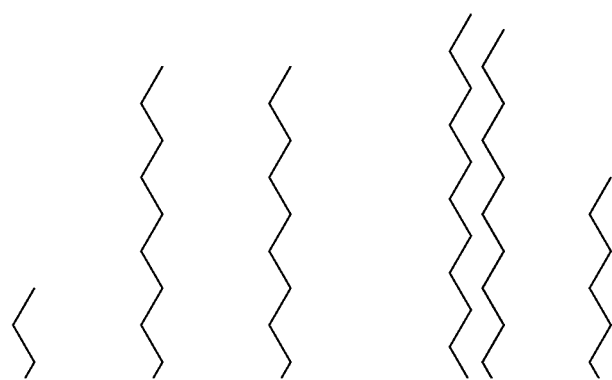
L

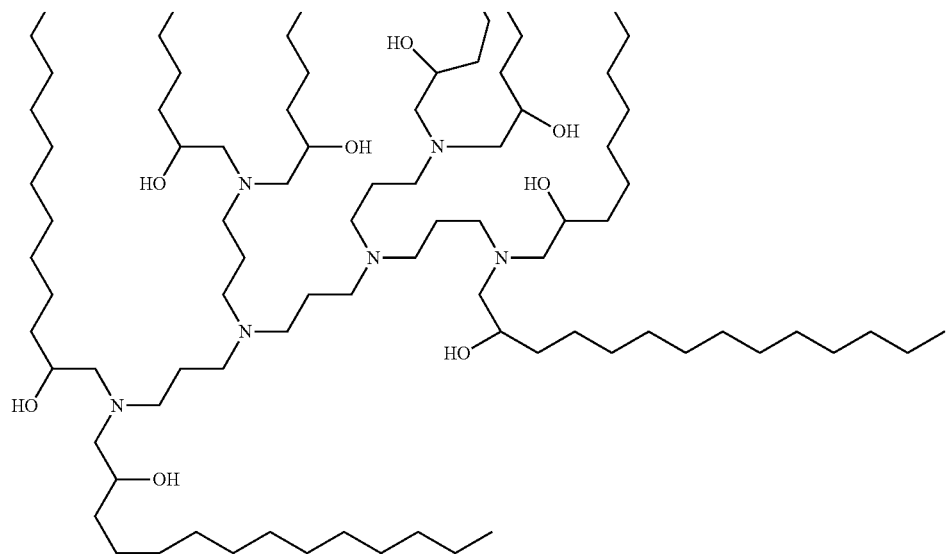
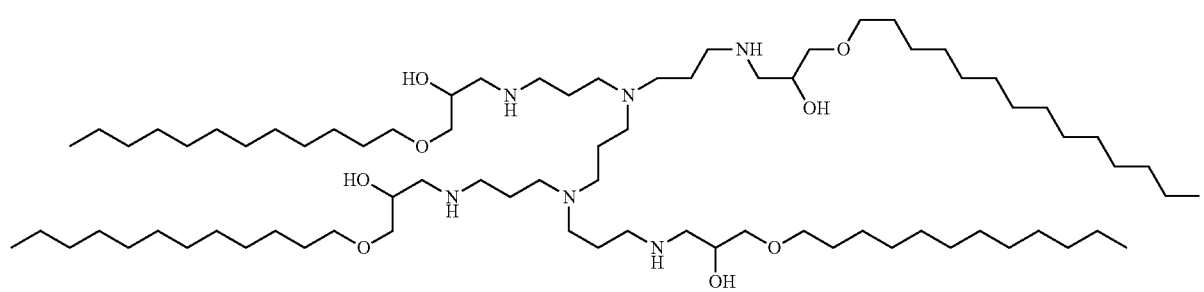
LI
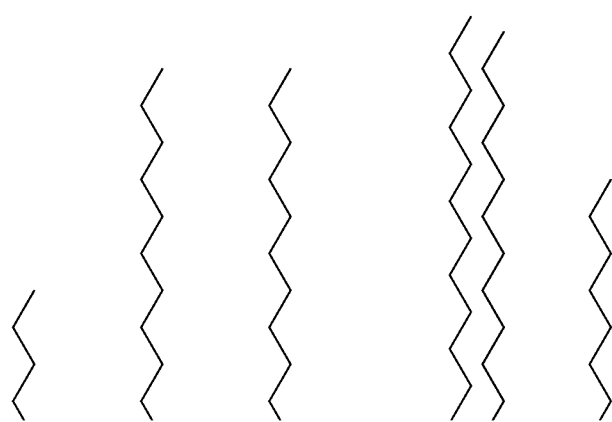
LII

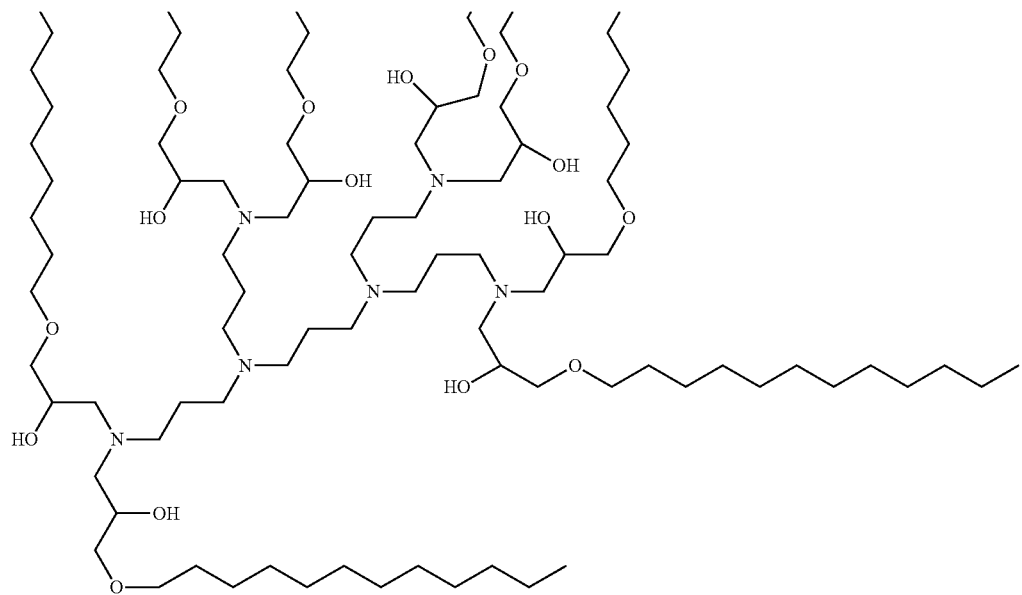
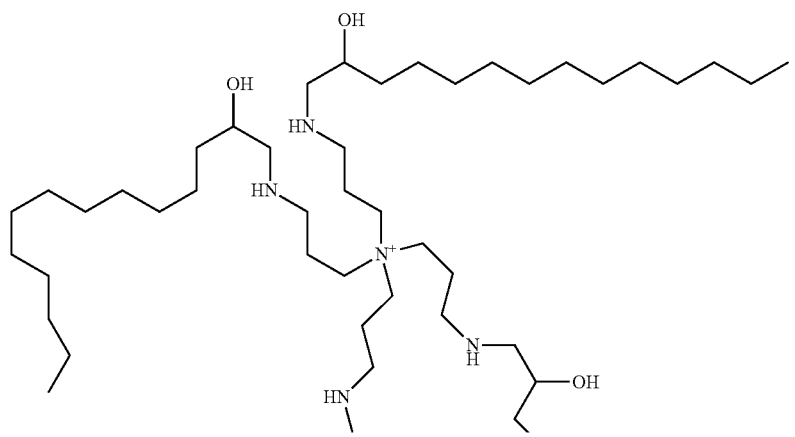
LIII
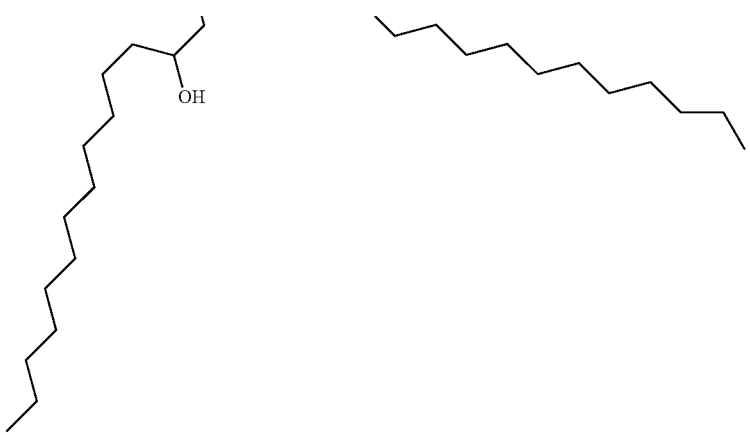

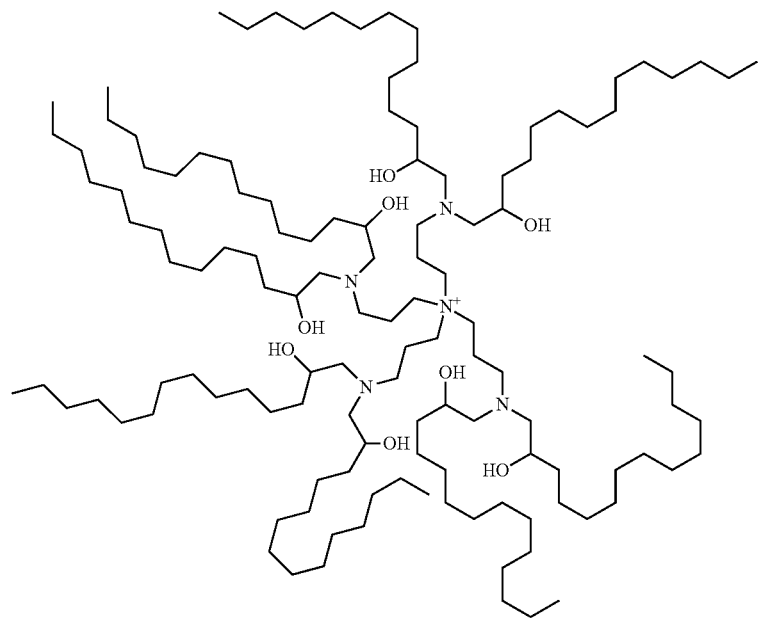
LIV
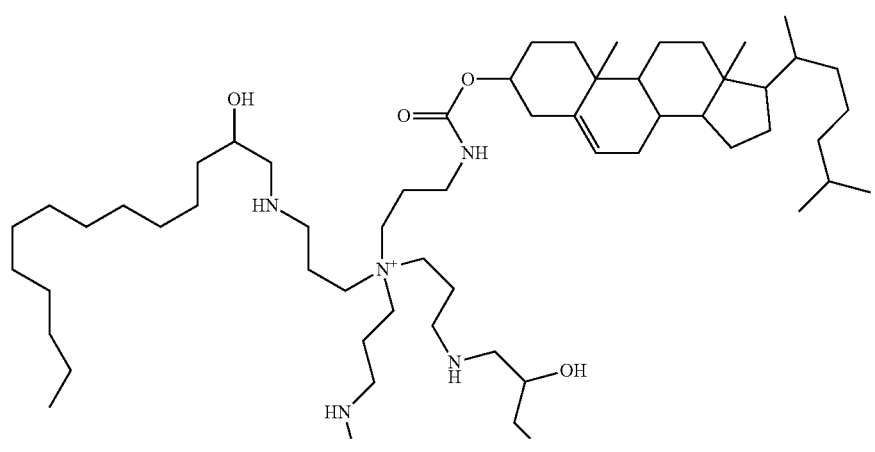
LV
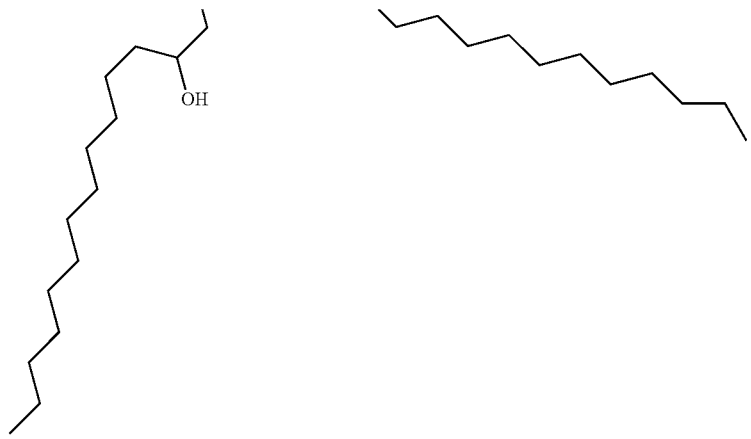

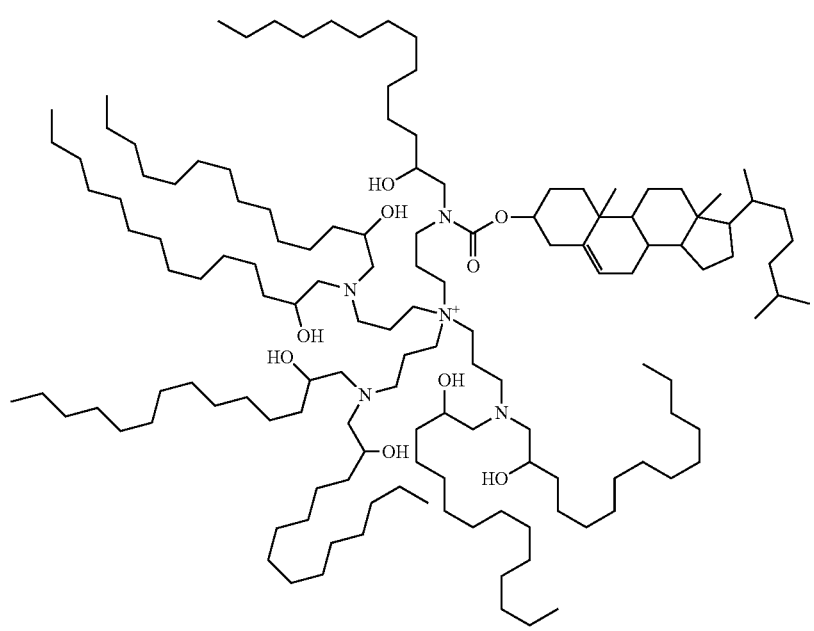
LVI
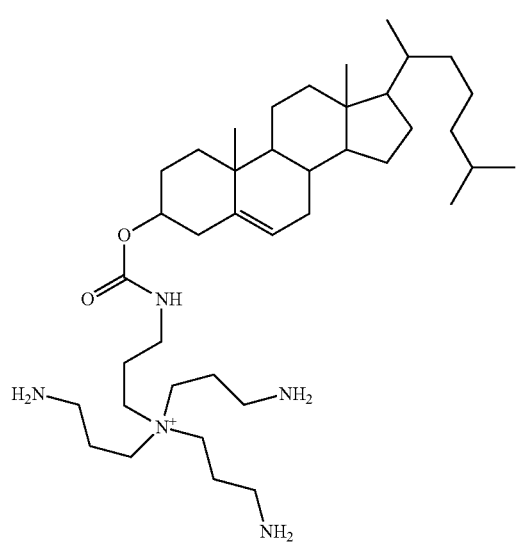
LVII
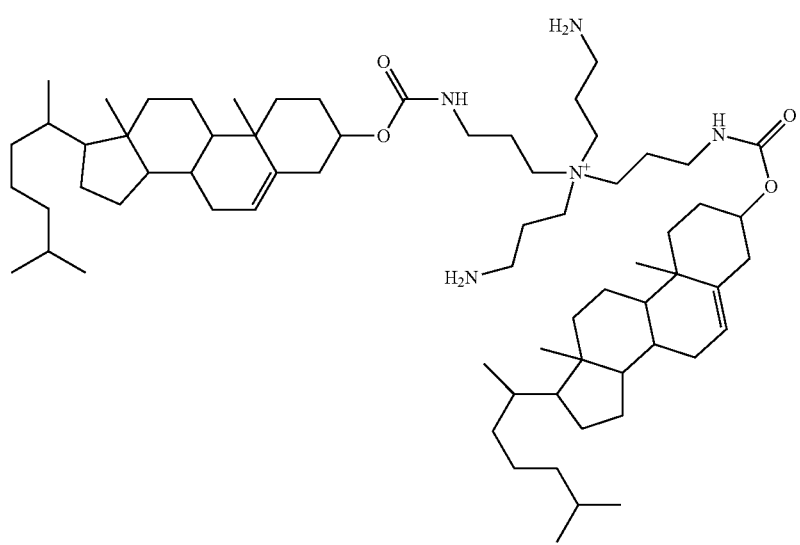
LVIII

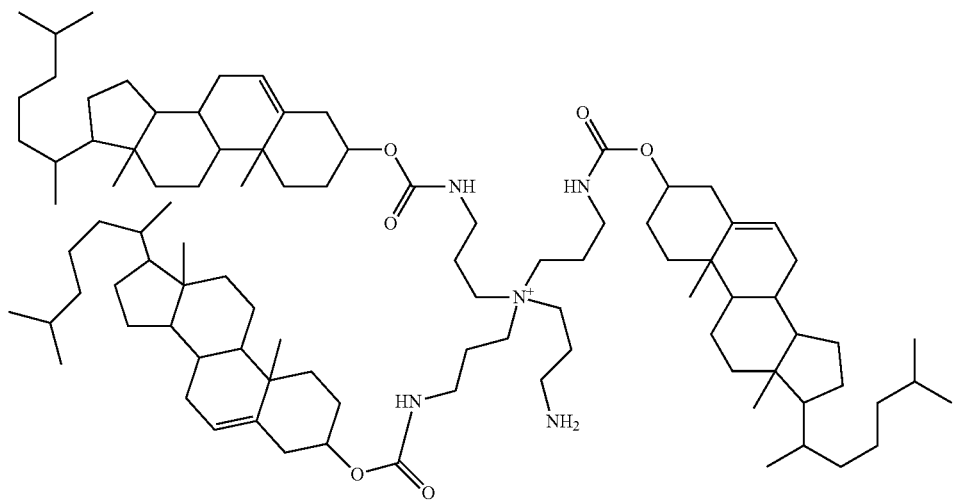
LIX
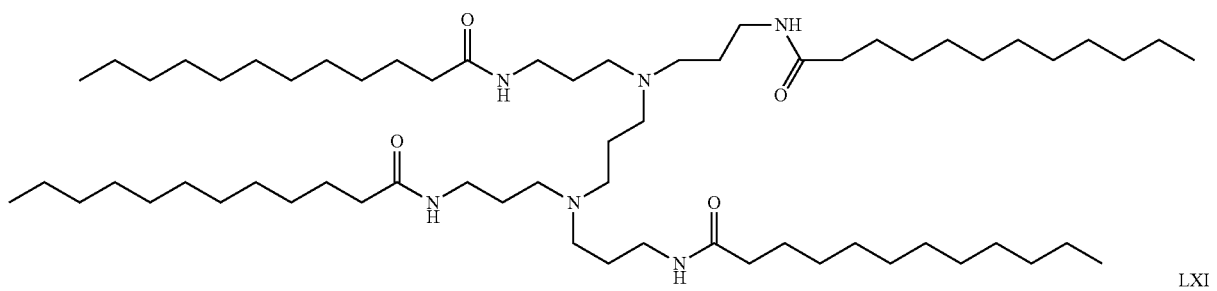
LX
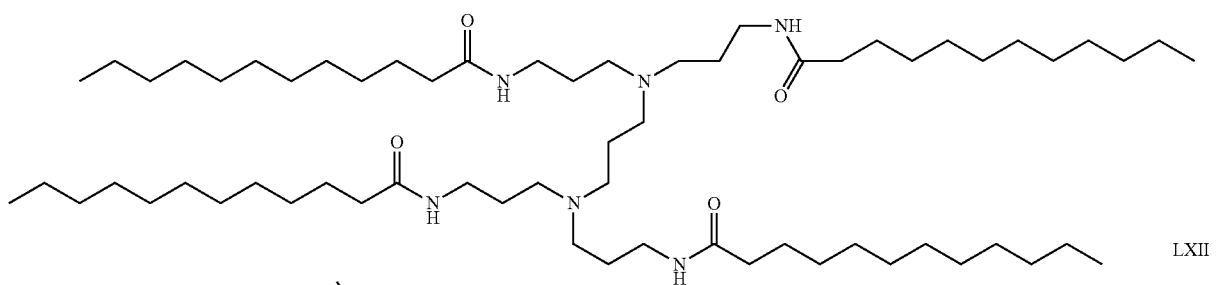
LXI
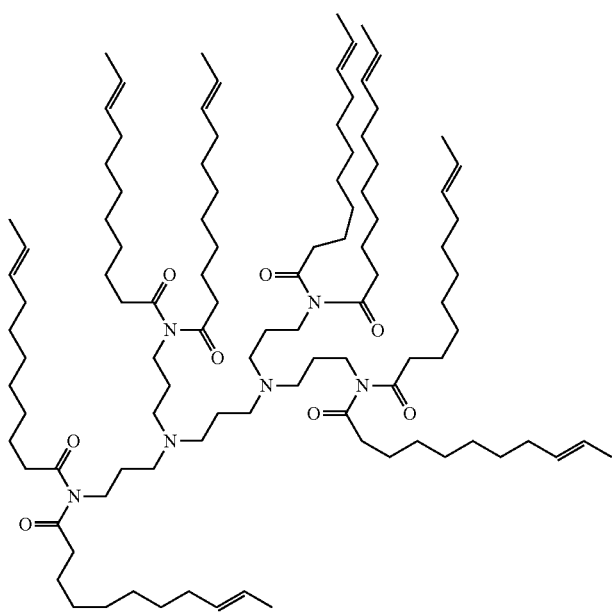
LXII

LXII
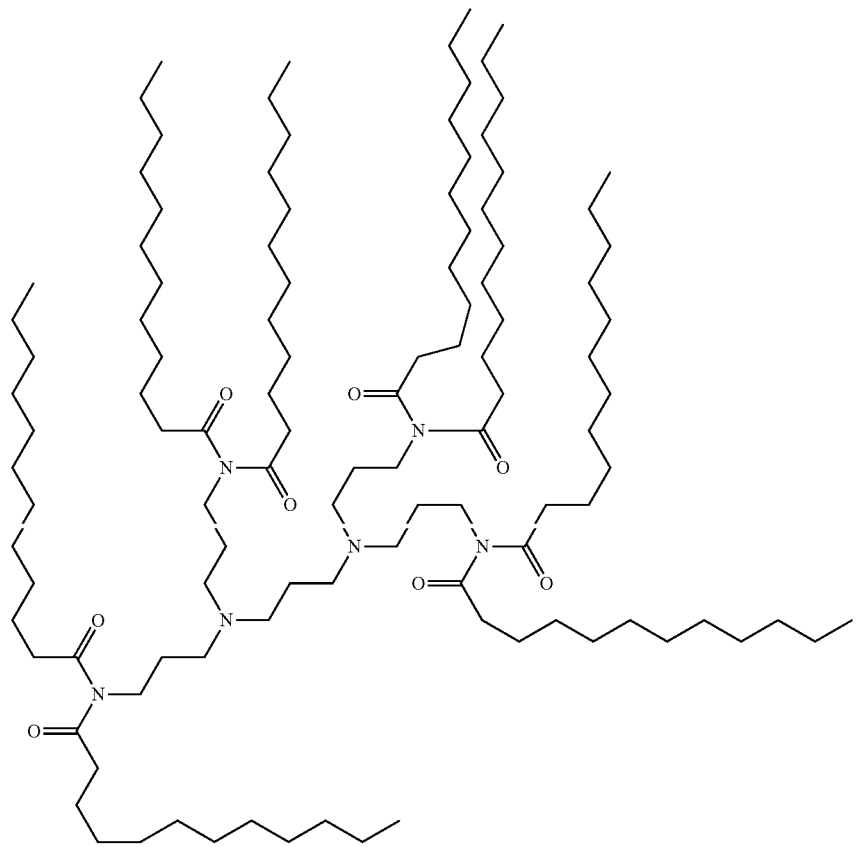
LXIII
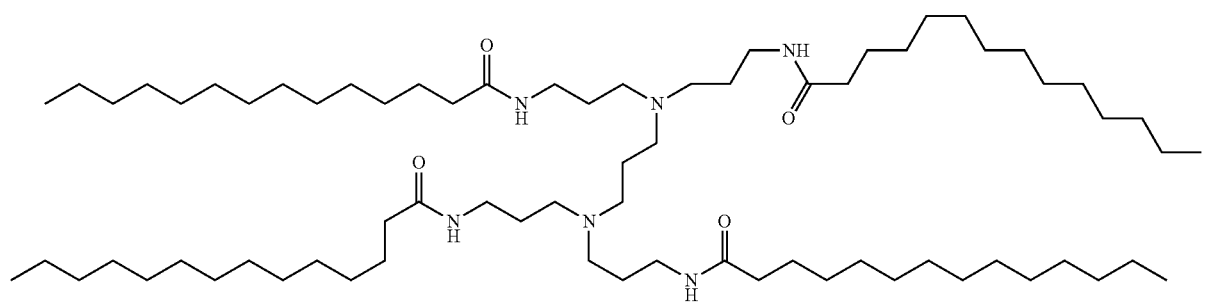
LXIV
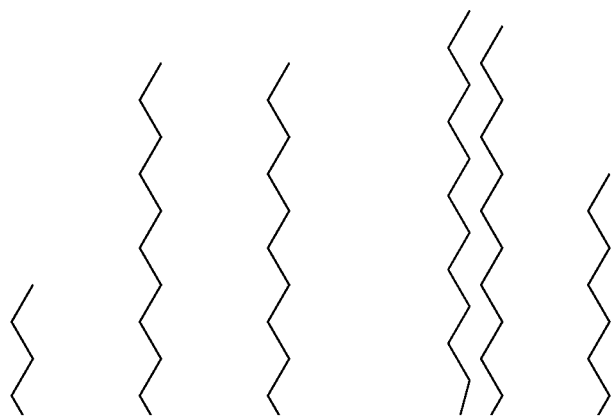

-continued
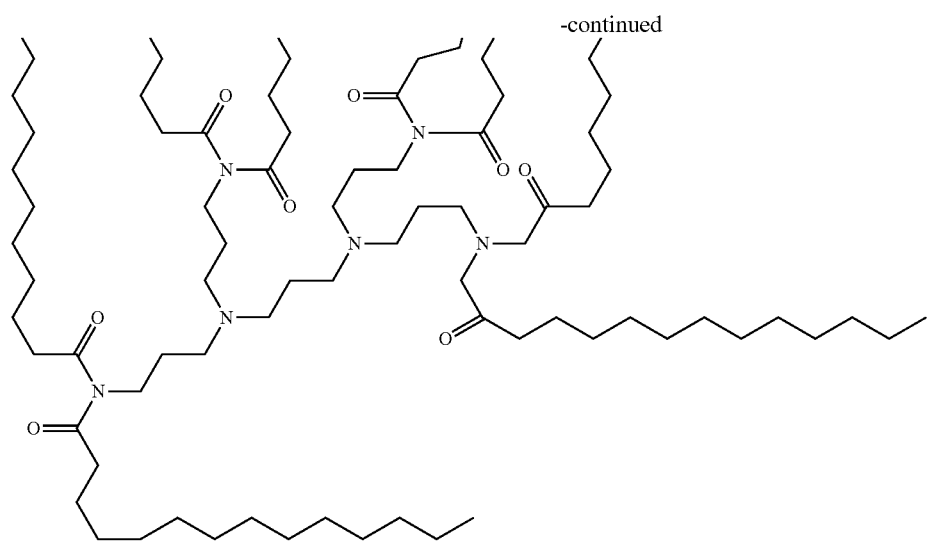
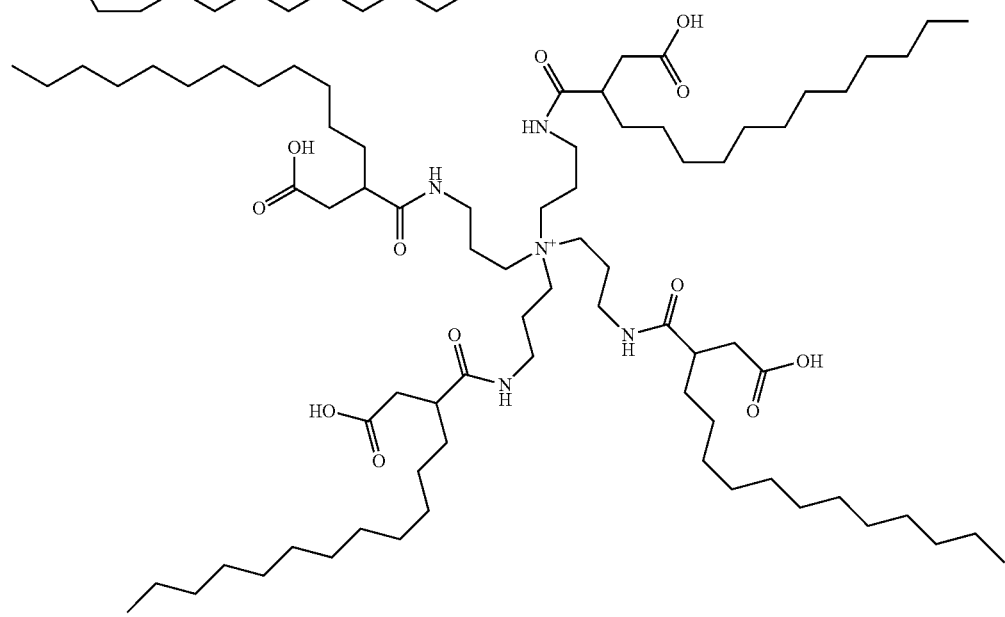
LXV
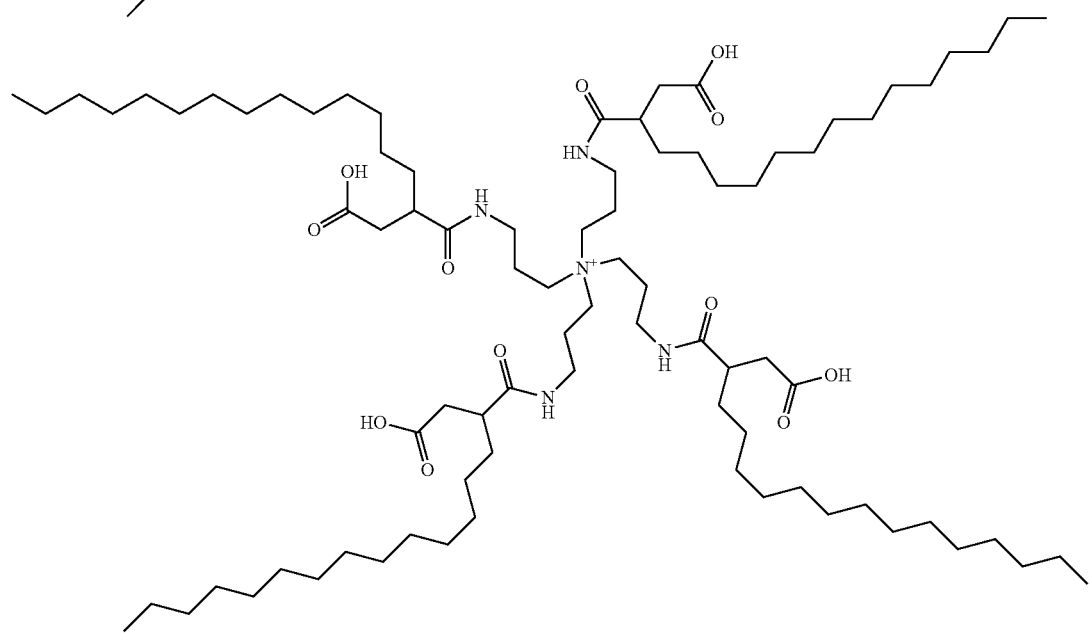
LXVI

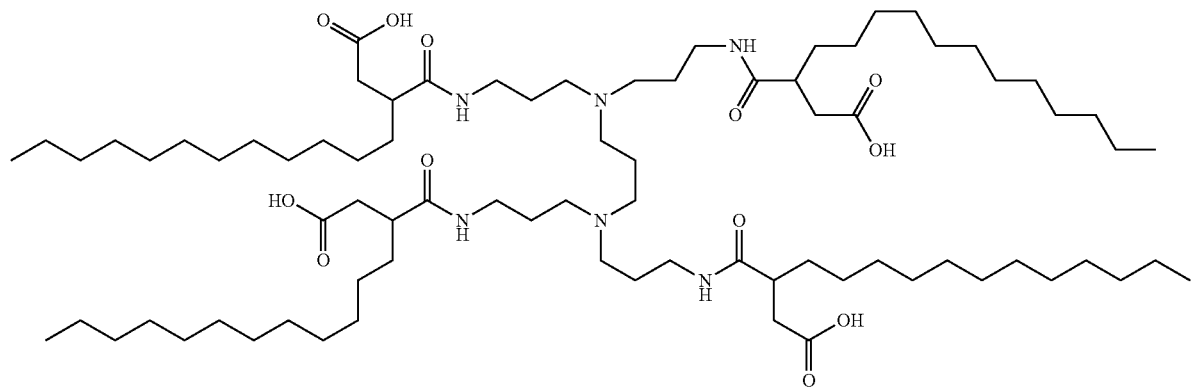

LXVII

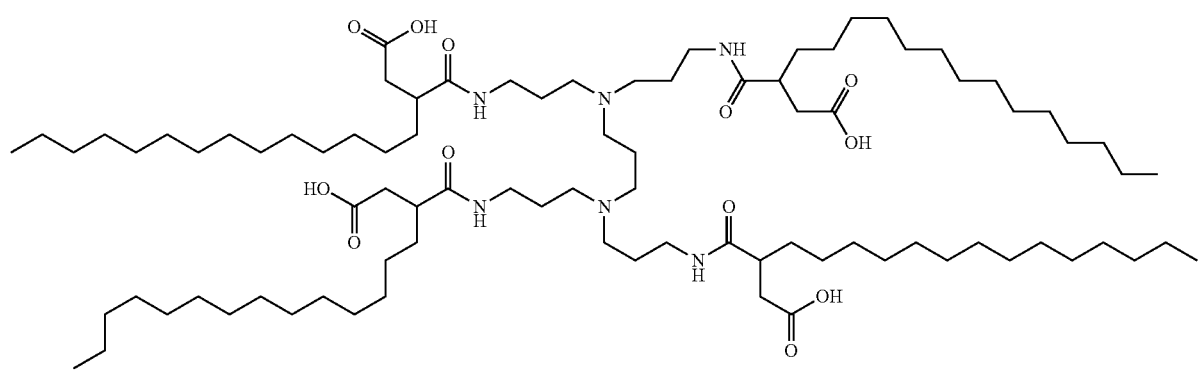

LXVIII

Examples of polyvalent cationic lipids polyamines such as N 6-tetrakis(3-aminopropyl)-1,3-propanediamine cholesteryl carbamate, and lipospermines that can be used include N4-spermine cholesteryl carbamate (GL-67), N4-spermidine cholesteryl carbamate (GL-53), 1-(N4-spermine)-2,3-dilaurylglycerol carbamate (GL-89), (dipalmitoylphosphatidylethanolamyl spermine, DPPES) dioctadecylamido glycylspermine (Transfectam, DOGS), 2,3-dioleyloxy-N-[2 (sperminecarboxamido)ethyl]-N,N-dimethyl-1-propanamonium trifluoroacetate. Lipospermines and lipospermidines are bifunctional molecules consisting of one or more hydrophobic chains covalently linked to a cationic grouping that has three or more amide hydrogens which can complex with a phosphate oxygen of a nucleic acid chain forming an ionic charge complex.

A preferred carbamate is a cholesterol-like compound: $N^6$-tetrakis(3-aminopropyl)-1,3-propanediamine cholesteryl carbamate, having the following structure:

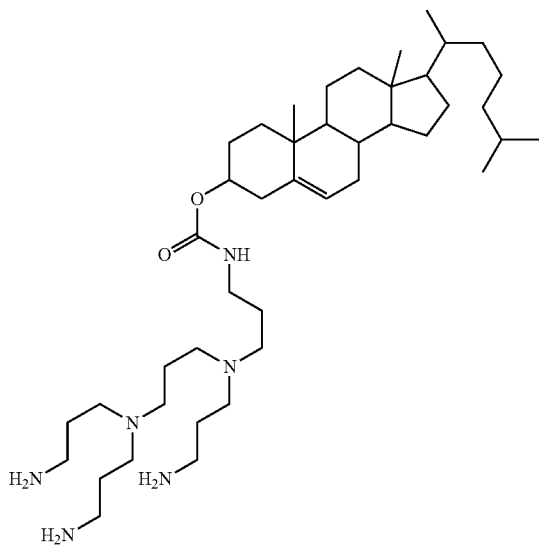 [SMILES: CC(C)CCCC(C)C1CCC2C3CC=C4CC(OC(=O)NCCCN(CCCN)CCCN(CCCN)CCCN)CCC4(C)C3CCC12C]

Neutral phospholipids include but are not limited to phosphatidyl ethanolamine, phosphatidyl cocaine, phosphatidyl inositol, sphinogomyelin, and diphosphatidyl glycerol. The phospholipid acyl (fatty acid) chains can consist of be saturated or with one or more unsaturated bond in either acyl chain thereof chain have individually, from 8 to about 26 carbons atoms, and as same (symmetry) or different (asymmetry). The double bonds in the acyl chains can be, independently, either cis or trans; with examples thereof including the 1-acyl and 2-acyl chains respectively, are independently selected from the group consisting of linoleoyl (18:2), linolenoyl (18:3), arachidonoyl (20:4) and docosahexaenoyl (22:6).

Sterols include cholesterol, lanosterol, 24-isopropylcholesterol, nicasterol, 7-dehydrocholesterol, 24-dehydrocholesterol, gorgosterol, dinosterol, 24S-hydroxycholesterol, and phytosterols, including ergosterol, stigmasterol, campesterol, fucosterol, β-sitosterol, and phytostanols, as well as sterol esters, steryl glycosides, and steryl alkyl ethers.

Sterol-PEG compounds are sterols linked to a polyethylene glycol (PEG) such as PEG-linked cholesterol in which the PEG is less than 5000 daltons, preferably less than 2000 daltons, most preferably between 200 and 1000 daltons.

The cationic lipid nucleic acid salts in a solid and stable form, in particular cationic lipid interfering nucleic acid salts used in the claimed formulations are produced by bringing into contact a solution of a cationic lipid with an aqueous solution of nucleic acid under conditions wherein the cationic lipid molecules complex with the nucleic acid to form a cationic lipid nucleic acid salt precipitate. Precipitation occurs for cationic organic molecules with a lipophilic moiety or a sufficient degree of hydrophobicity to render the nucleic acid insoluble in water. The resulting precipitate contains an amount of the cationic lipid molecular positive charge in a ratio which brings down nucleic acid from complete hydrophilic to less hydrophilic or rendering nucleic acid partially or completely hydrophobic, preferably one to one molar concentration with the number of nucleotides present in the nucleic acid. The nucleic acid salt organic cationic lipid precipitate can be recovered from the aqueous liquors using filtration, centrifugation and other methods available to those skilled in the art of chemical process. The precipitated cationic lipid salt can be dried and subjected to numerous mechanical treatments to render it suitable for incorporation into solid and liquid dosage forms of nucleic acid drugs.

Formulations are then produced by mixing the cationic lipid nucleic acid salt with one or more lipids, including another cationic lipid an amphiphile such as N 6-tetrakis(3-aminopropyl)-1,3-propanediamine cholesteryl carbamate, a phospholipid, a hydrophobic lipid preferably a sterol including cholesterol, and a PEG-linked lipid, preferably a PEG-linked sterol.

A polyethylene glycol (PEG)-linked lipid includes a PEG-linked cholesterol and PEG-linked derivatives of cholesterol and PEG-linked phytosterols such as PEG-campesterol, PEG-sitosterol and PEG-stigmasterol, DSPE-PEG, DOPE-PEG, and ceramide-PEG.

This disclosure provides pharmaceutically acceptable nucleic acid compositions useful for therapeutic delivery of nucleic acids, plasmids, antisense nucleic acids, ribozymes, aptamers, antagomirs, siRNA, miRNA, gene-silencing interfering nucleic acids and mixtures thereof. These compositions and methods may be used for prevention and/or treatment of diseases in a mammal.

The claimed lipid/nucleic acid formulations can be made by re-suspending cationic lipid nucleic acid salts in an organic or aprotic solvent and upon mixing with other lipids and further process, such as evaporation of solvent, produce nucleic acid lipid complexes that can be administered to an individual for gene therapies using plasmid DNA as the nucleic acid, or for down-regulating a gene using antisense, ribozymes, antagomirs, siRNA, miRNA, iNA, or to inhibit other conditions using aptamers as the nucleic acid.

The present disclosure also satisfies these needs and fulfills additional objects and advantages by providing for a self-emulsifying complex of lipids and nucleic acid that has a monodispersed particle size distribution under 600 nm, preferably under 400 nm, most preferably under 200 nm.

Compositions and Formulations for Administration

The nucleic acid-lipid compositions of this disclosure may be administered by various routes, for example, to effect systemic delivery via intravenous, parenteral, intraperitoneal or topical routes. In some embodiments, a siRNA may be delivered intracellularly, for example, in cells of a target tissue such as lung or liver, or in inflamed tissues. In some embodiments, this disclosure provides a method for delivery of siRNA in vivo. A nucleic acid-lipid composition may be administered intravenously, subcutaneously, or intraperitoneally to a subject. In some embodiments, the disclosure provides methods for in vivo delivery of interfering RNA to the lung of a mammalian subject.

In some embodiments, this disclosure provides a method of treating a disease or disorder in a mammalian subject. A therapeutically effective amount of a composition of this disclosure containing a nucleic, a cationic lipid, an amphiphiles, a phospholipid, cholesterol and a PEG-linked cholesterol may be administered to a subject having a disease or disorder associated with expression or overexpression of a gene that can be reduced, decreased, downregulated, or silenced by the composition.

The compositions and methods of the disclosure may be administered to subjects by a variety of mucosal administration modes, including by oral, rectal, vaginal, intranasal, intrapulmonary, or transdermal or dermal delivery, or by topical delivery to the eyes, ears, skin or other mucosal surfaces. In some aspects of this disclosure, the mucosal tissue layer includes an epithelial cell layer. The epithelial cell can be pulmonary, tracheal, bronchial, alveolar, nasal, buccal, epidermal, or gastrointestinal. Compositions of this disclosure can be administered using conventional actuators such as mechanical spray devices, as well as pressurized, electrically activated, or other types of actuators.

Compositions of this disclosure may be administered in an aqueous solution as a nasal or pulmonary spray and may be dispensed in spray form by a variety of methods known to those skilled in the art. Pulmonary delivery of a composition of this disclosure is achieved by administering the composition in the form of drops, particles, or spray, which can be, for example, aerosolized, atomized, or nebulized. Particles of the composition, spray, or aerosol can be in a either liquid or solid form. Preferred systems for dispensing liquids as a nasal spray are disclosed in U.S. Pat. No. 4,511,069. Such formulations may be conveniently prepared by dissolving compositions according to the present disclosure in water to produce an aqueous solution, and rendering said solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien ed., Elsevier Publishers, New York, 1985; and in U.S. Pat. No. 4,778,810. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or mixtures thereof.

Nasal and pulmonary spray solutions of the present disclosure typically comprise the drug or drug to be delivered, optionally formulated with a surface active agent, such as a nonionic surfactant (e.g., polysorbate-80), and one or more buffers. In some embodiments of the present disclosure, the nasal spray solution further comprises a propellant. The pH of the nasal spray solution may be from about pH 6.8 to 7.2. The pharmaceutical solvents employed can also be a slightly acidic aqueous buffer of pH 4-6. Other components may be added to enhance or maintain chemical stability, including preservatives, surfactants, dispersants, or gases.

In some embodiments, this disclosure is a pharmaceutical product which includes a solution containing a composition of this disclosure and an actuator for a pulmonary, mucosal, or intranasal spray or aerosol.

A dosage form of the composition of this disclosure can be liquid, in the form of droplets or an emulsion, or in the form of an aerosol.

A dosage form of the composition of this disclosure can be solid, which can be reconstituted in a liquid prior to administration. The solid can be administered as a powder. The solid can be in the form of a capsule, tablet or gel.

To formulate compositions for pulmonary delivery within the present disclosure, the biologically active agent can be combined with various pharmaceutically acceptable additives, as well as a base or carrier for dispersion of the active agent(s). Examples of additives include pH control agents such as arginine, sodium hydroxide, glycine, hydrochloric acid, citric acid, and mixtures thereof. Other additives include local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione). When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g., methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters 4 such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

Formulations for mucosal, nasal, or pulmonary delivery may contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10,000 and preferably not more than 3000. Examples of hydrophilic low molecular weight compounds include polyol compounds, such as oligo-, di- and monosaccarides including sucrose, mannitol, lactose, L-arabinose, D-erythrose, D-ribose, D-xylose, D-mannose, D-galactose, lactulose, cellobiose, gentibiose, glycerin, polyethylene glycol, and mixtures thereof. Further examples of hydrophilic low molecular weight compounds include N-methylpyrrolidone, alcohols (e.g., oligovinyl alcohol, ethanol, ethylene glycol, propylene glycol, etc.), and mixtures thereof.

The compositions of this disclosure may alternatively contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the biologically active agent may be administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the disclosure can be brought about by including in the composition agents that delay absorption, for example, aluminum monosterate hydrogels and gelatin.

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

While this invention has been described in relation to certain embodiments, and many details have been set forth for purposes of illustration, it will be apparent to those skilled in the art that this invention includes additional embodiments, and that some of the details described herein may be varied considerably without departing from this invention. This invention includes such additional embodiments, modifications and equivalents. In particular, this invention includes any combination of the features, terms, or elements of the various illustrative components and examples.

EXAMPLES

Examples 1-4

Nucleic Acid/Cationic Lipid Salts

A nucleic acid/cationic lipid salt was prepared by the following method. Two mg of the cationic lipid was dissolved in 0.1 mL of chloroform in a clean, dry borosilicate clear glass vial and the chloroform was evaporated off by blowing nitrogen gas into the vial and any remaining trace amount of chloroform was removed by drying in vacuo in a vacuum chamber. The vial was removed from the vacuum chamber and 0.1 mL of ethanol was added. The vial was sealed with TEFLON®-lined cap and tightly wrapped with a sealing tape. The vial was vortexed or/and sonicated to dissolve the cationic lipid.

The solution of the cationic lipid in ethanol was added to an aqueous solution containing 1 mg siRNA. The addition of the cationic lipid to the siRNA solution caused immediate aggregation forming a water-insoluble cationic lipid/nucleic acid salt comprised of the cationic lipid and siRNA.

The water-insoluble cationic lipid/nucleic acid salt in a tube was then centrifuged in an Eppendorf microcentrifuge at maximum speed for 15 minutes to form a pellet. The supernatant after each centrifugation were collected and the amount siRNA in the supernatant was measured with OD260.

For the remaining examples, the nucleic acid/cationic lipid salt is solubilized in an organic solvent to be mixed with additional lipids into a formulation.

Table 1 lists cationic lipids that were used to form nucleic acid/cationic lipid salts using this method.

TABLE 1

| Example 1 | DOTMA (N-[1-(2,3-dioleyloxy)propyl]-N,N,N-trimethylammonium chloride) |
| Example 2 | DC-Chol (cholesteryl 3β-N-(dimethylaminoethyl)carbamate hydrochloride) |
| Example 3 | DODAP (1,2-dimyristoyl-3-dimethylammonium propane) |
| Example 4 | DOTAP (N-(l-(2,3-dioleoyloxy)propyl)-N,N,N-trimethylammonium chloride) |

Table 2 is the summary of measurement of the ratio of siRNA/lipid which rendering siRNA insoluble in water.

TABLE 2

| siRNA/lipids ratio | siRNA remaining in water | | | |
| | DOTAP | DODAP | DC-Chol | DOTMA |
| --- | --- | --- | --- | --- |
| 0 | 100 | 100 | 100 | 100 |
| 0.5 | 63 | 56 | 72 | 61 |
| 0.75 | 55 | 52 | 63 | 57 |
| 1 | 45 | 46 | 57 | 46 |
| 1.5 | 28 | 30 | 35 | 29 |
| 2 | 10 | 12 | 13 | 6 |

Examples 5-18

Liver siRNA Delivery Formulation

A liver siRNA delivery formulation was prepared by the following method. After centrifuging and drying the cationic lipid/siRNA salt (containing 1 mg siRNA in complexed with the cationic lipid) which was made as Examples 1-4, the salt was re-suspended in 100 µL of chloroform and mixed with the a mixture of lipids in chloroform: 4.4 mg carbamate, 2.7 to 4.4 mg phospholipid, 3.2 mg cholesterol, and 14.4 mg lipid-PEG, according to the specific carbamate, phospholipid and lipid-PEG identified in Table 3. The mixture was dried under vacuum and stored at 4° C. until use. Before injection, 9% sucrose solution was added with shaking to form an isotonic and a self-emulsifying siRNA/lipid suspension of siRNA/lipid formulation. The formulation was dosed to CD1 mice via tail vein at dose volume of 0.2 ml. Two days later, the mice were sacrificed and liver was harvested for analyzing gene expression by real-time RT-PCR method. Greater than 80% silencing of the targeted gene was observed at a siRNA dose of 2 mg/kg.

TABLE 3

Liver Delivery Formulations

| | cationic lipid | carbamate | neutral phospholipid | sterol-PEG |
| --- | --- | --- | --- | --- |
| Example 5 | DOTMA | N6-tetrakis(3-aminopropyl)-1,3-propanediamine cholesteryl | 1,2-diarachidonoyl-sn-glycero-3-phosphoethanolamine | cholesterol-PEG 1000 |
| Example 6 | DC-Chol | N6-tetrakis(3-aminopropyl)-1,3-propanediamine cholesteryl | 1,2-diarachidonoyl-sn-glycero-3-phosphoethanolamine | cholesterol-PEG 1000 |
| Example 7 | DOTMA | N6-tetrakis(3-aminopropyl)-1,3-propanediamine cholesteryl | 1,2-didocosahexaenoyl-sn-glycero-3-phosphoethanolamine | cholesterol-PEG 1000 |
| Example 8 | DC-Chol | N6-tetrakis(3-aminopropyl)-1,3-propanediamine cholesteryl | 1,2-didocosahexaenoyl-sn-glycero-3-phosphoethanolamine | cholesterol-PEG 1000 |
| Example 9 | DOTMA | N6-tetrakis(3-aminopropyl)-1,3-propanediamine cholesteryl | 1,2-didocosahexaenoyl-sn-glycero-3-phosphoethanolamine | cholesterol-PEG 660 |

TABLE 3-continued

Liver Delivery Formulations

| | cationic lipid | carbamate | neutral phospholipid | sterol-PEG |
|---|---|---|---|---|
| Example 10 | DC-Chol | $N^6$-tetrakis(3-aminopropyl)-1,3-propanediamine cholesteryl | 1,2-didocosahexaenoyl-sn-glycero-3-phosphoethanolamine | cholesterol-PEG 660 |
| Example 11 | DOTMA | $N^6$-tetrakis(3-aminopropyl)-1,3-propanediamine cholesteryl | 1,2-dilinoleoyl-sn-glycero-3-phosphoethanolamine | cholesterol-PEG 660 |
| Example 12 | DC-Chol | $N^6$-tetrakis(3-aminopropyl)-1,3-propanediamine cholesteryl | 1,2-dilinoleoyl-sn-glycero-3-phosphoethanolamine | cholesterol-PEG 660 |
| Example 13 | DOTMA | $N^6$-tetrakis(3-aminopropyl)-1,3-propanediamine cholesteryl | 1,2-dilinoleoyl-sn-glycero-3-phosphoethanolamine | cholesterol-PEG 1000 |
| Example 14 | DOTMA | $N^6$-tetrakis(3-aminopropyl)-1,3-propanediamine cholesteryl | 1,2-dilinoleoyl-sn-glycero-3-phosphoethanolamine | ceramide C16 PEG 750 |
| Example 15 | DOTMA | $N^4$-spermine cholesteryl carbamate | 1,2-dilinoleoyl-sn-glycero-3-phosphoethanolamine | cholesterol-PEG 1000 |
| Example 16 | DOTMA | $N^4$-spermine cholesteryl carbamate | 1,2-didocosahexaenoyl-sn-glycero-3-phosphoethanolamine | cholesterol-PEG 1000 |
| Example 17 | DOTMA | $N^6$-tetrakis(3-aminopropyl)-1,3-propanediamine cholesteryl | 1,2-dilinoleoyl-sn-glycero-3-phosphoethanolamine | DSPE-PEG 2000 |
| Example 18 | DOTMA | $N^6$-tetrakis(3-aminopropyl)-1,3-propanediamine cholesteryl | 1,2-dilinoleoyl-sn-glycero-3-phosphoethanolamine | DOPE-PEG 2000 |
| Example 19 | DOTMA | Spermine cholesteryl carbamate | 1,2-diarachidonoyl-sn-glycero-3-phosphoethanolamine | cholesterol-PEG 1000 |

FIG. 1 describes the results of testing the formulation of Example 11 by injection into mice. The results show that injection of ApoB siRNA in the claimed formulation is effective in knocking down expression of ApoB gene expression in liver and in lowering serum cholesterol levels at a dosage of 0.5-4 mg siRNA/kg.

Figure 2:
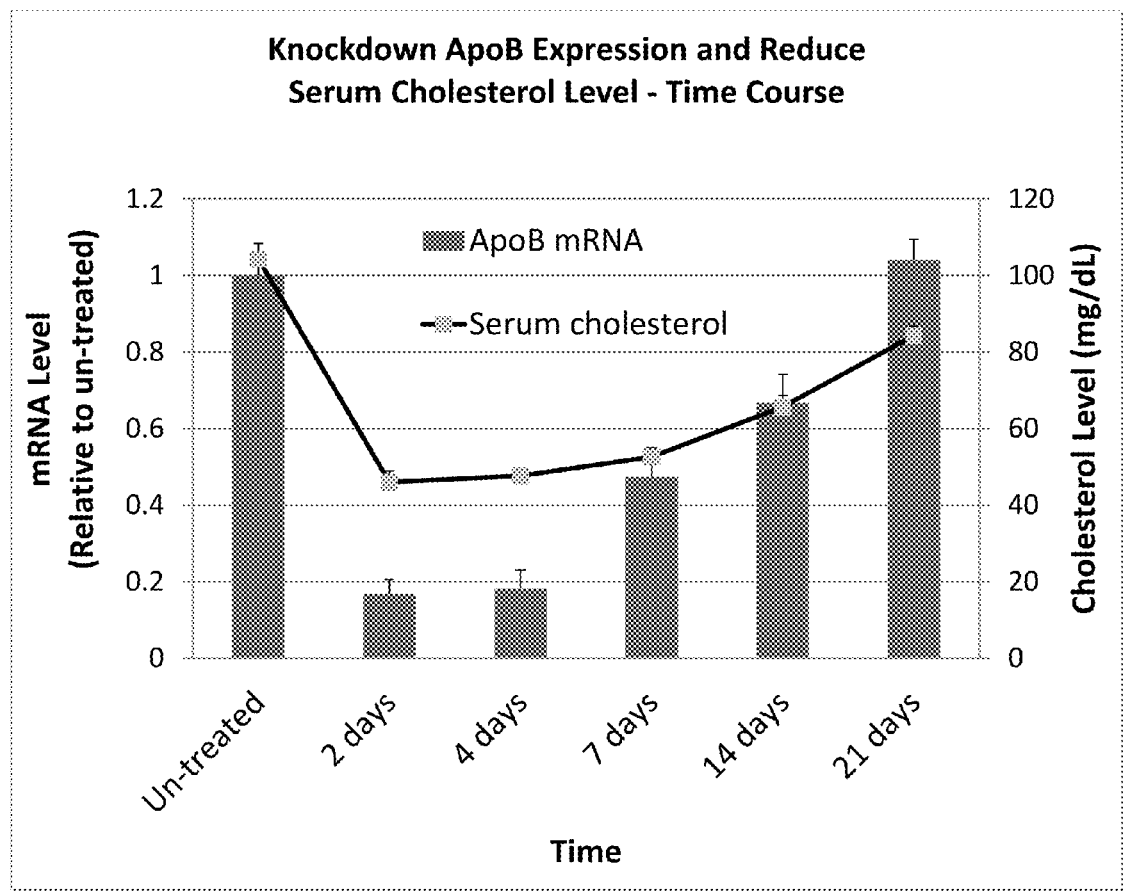

FIG. 2 shows the time course of the response of the body to ApoB siRNA in the claimed formulation of Example 11. The results show that ApoB miRNA expression and serum cholesterol are lowered up to 14 days after an injection.

Example 20-25

Lung siRNA Delivery Formulation

A lung siRNA delivery formulation was prepared by the following method. After centrifuging and drying the cationic lipid/siRNA salt (containing 1 mg siRNA in complexed with the cationic lipid) which was made as Examples 1-4, the salt was re-suspended in 100 μL of chloroform and mixed with the a mixture of lipids in chloroform as follows: 8.8 mg carbamate, 2.2 mg phospholipid, 1.6 mg cholesterol, and 14.4 mg lipid-PEG, according to the specific carbamates, phospholipids and lipid-PEGs identified in Table 4. The mixture was dried under vacuum and stored at 4° C. until use. Before injection, 9% sucrose solution was added with shaking to form an isotonic and a self-emulsifying siRNA/lipid suspension of siRNA/lipid formulation. The formulation was dosed to 129S1/svImJ mice via tail vein at dose volume of 0.2 ml. Two days later, the mice were sacrificed. The lung and liver was harvested for analyzing gene expression by real-time RT-PCR method.

TABLE 4

Lung Delivery Formulations

| | Cationic lipid | carbamate | Phospholipid | lipid-PEG |
|---|---|---|---|---|
| Example 20 | DOTMA | $N^6$-tetrakis(3-aminopropyl)-1,3-propanediamine cholesteryl carbamate | 1,2-dilinoleoyl-sn-glycero-3-phosphoethanolamine | cholesterol-PEG 660 |

TABLE 4-continued

Lung Delivery Formulations

| | Cationic lipid | carbamate | Phospholipid | lipid-PEG |
|---|---|---|---|---|
| Example 21 | DOTMA | $N^6$-tetrakis(3-aminopropyl)-1,3-propanediamine cholesteryl carbamate | 1,2-dilinoleoyl-sn-glycero-3-phosphoethanolamine | cholesterol-PEG 1000 |
| Example 22 | DOTMA | $N^4$-spermine cholesteryl carbamate | 1,2-dilinoleoyl-sn-glycero-3-phosphoethanolamine | cholesterol-PEG 660 |
| Example 23 | DOTMA | $N^6$-tetrakis(3-aminopropyl)-1,3-propanediamine cholesteryl carbamate | 1,2-didocosahexaenoyl-sn-glycero-3-phosphoethanolamine | cholesterol-PEG 660 |
| Example 24 | DOTMA | $N^6$-tetrakis(3-aminopropyl)-1,3-propanediamine cholesteryl carbamate | 1,2-diarachidonoyl-sn-glycero-3-phosphoethanolamine | cholesterol-PEG 660 |
| Example 25 | DOTMA | Spermine cholesteryl carbamate | 1,2-diarachidonoyl-sn-glycero-3-phosphoethanolamine | cholesterol-PEG 1000 |

Figure 3A:
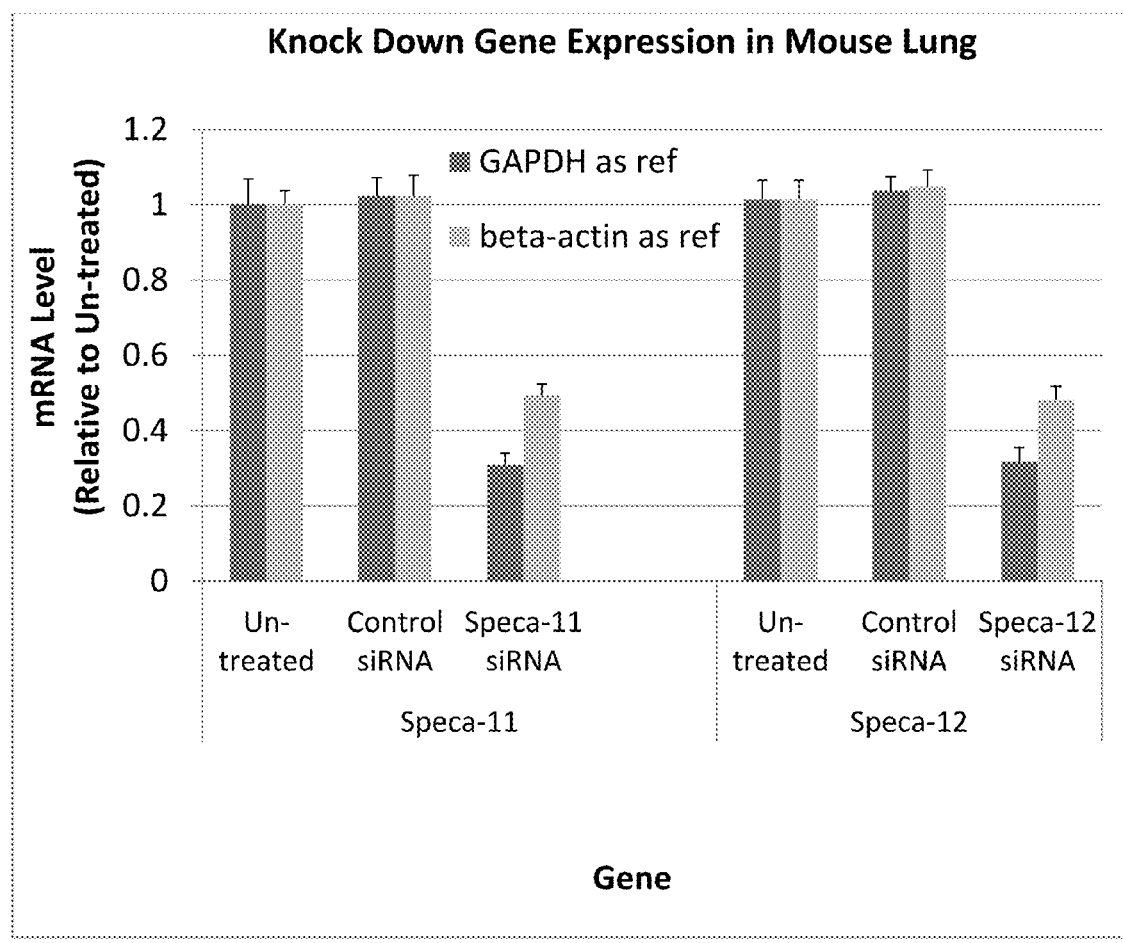
FIG. 3. 129S1/svImJ mice were administered intravenously with a single dose of a lung specific delivery formulation for siRNA at dosing volume of 0.2 ml (4 mg/kg siRNA). Three days later, the lung and liver were harvested for analyzing gene expression with real-time RT-PCR method (GAPDH and beta-actin as reference genes). Each data point represents the mean+SEM (n=5). The expression level of the targeted genes was significantly knocked down in lung (A), but not in liver (B). Speca-11 and Speca-12 are the siRNAs targeting different genes.
Figure 3B:
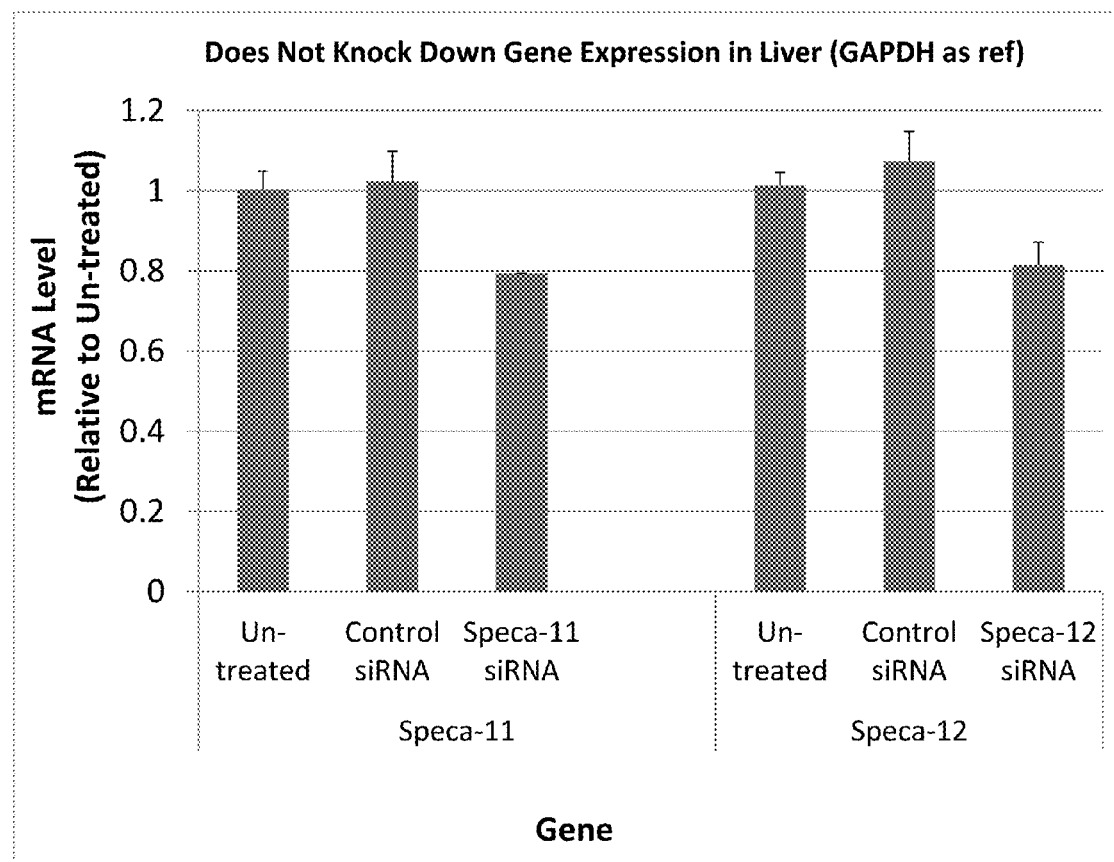

FIG. 3 describes the results of testing a claimed formulation by injection into mice. The results show that injection of GAPDH siRNA and β-Actin in the formulation of Example 20 is effective in knocking down expression of the corresponding genes in lung, but that this formulation only minimally changed expression of these genes in liver.

Figure 4:
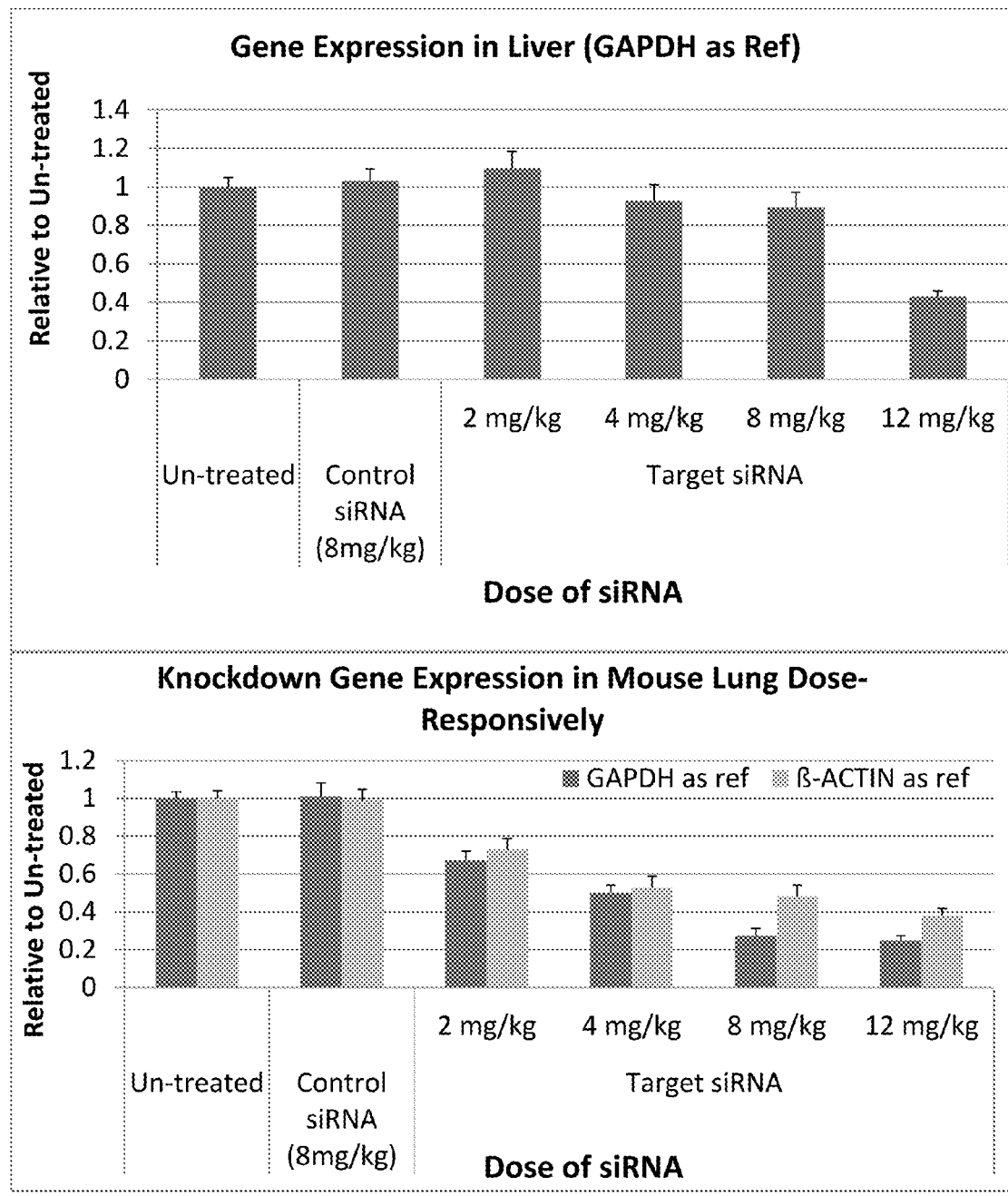
FIG. 4. 129S1/svImJ mice were administered a single dose of 0.2 ml formulated siRNA intravenously at the indicated dose level. Three days later, the lung (A) and liver (B) were harvested for analyzing gene expression with real-time RT-PCR method (GAPDH and beta-actin as reference genes). Each data point represents the mean+SEM (n=5). The expression level of the targeted genes was knocked down in lung in a dose-responsive manner.

FIG. 4 shows the dose response of the lung to injections of GAPDH siRNA and β-Actin ApoB siRNA in the claimed formulation of Example 20. The results show that expression of these are lowered by a dosage of 2-12 mg siRNA/kg, and that these dosages of 2-8 mg siRNA/kg minimally affect liver expression.

Example 26-32

Tumor siRNA Delivery Formulation

A tumor siRNA delivery formulation was prepared by the following method. After centrifuging and drying the cationic lipid/siRNA salt (containing 1 mg siRNA in complexed with the cationic lipid) which was made as Examples 1-4, the salt was re-suspended in 100 μL of chloroform and mixed with the a mixture of lipids in chloroform as follows: 4.4 mg carbamate, 4.4 mg phospholipid, 2.4 mg cholesterol, and 21.6 mg lipid-PEG, according to the specific carbamates, phospholipids and lipid-PEGs identified in Table 5. The mixture was dried under vacuum and stored at 4° C. until use. Before injection, 9% sucrose solution was added with shaking to form an isotonic and a self-emulsifying siRNA/lipid suspension of siRNA/lipid formulation. The formulation was dosed to Balb/c mice via tail vein at dose volume of 0.2 ml. The mice was implanted with EMT6 cells into liver five days before dosing the siRNA formulation. Two days later, the mice were sacrificed. The tumor and liver were harvested for analyzing gene expression by real-time RT-PCR method.

TABLE 5

Tumor Delivery Formulations

| | Cationic lipid | carbamate | Phospholipid | lipid-PEG |
|---|---|---|---|---|
| Example 26 | DOTMA | $N^6$-tetrakis(3-aminopropyl)-1,3-propanediamine cholesteryl carbamate | 1,2-dilinoleoyl-sn-glycero-3-phosphoethanolamine | cholesterol-PEG 660 |
| Example 27 | DOTMA | $N^6$-tetrakis(3-aminopropyl)-1,3-propanediamine cholesteryl carbamate | 1,2-dilinoleoyl-sn-glycero-3-phosphoethanolamine | cholesterol-PEG 1000 |
| Example 28 | DOTMA | $N^6$-tetrakis(3-aminopropyl)-1,3-propanediamine cholesteryl carbamate | 1,2-dilinoleoyl-sn-glycero-3-phosphoethanolamine | DSPE-PEG 2000 |

TABLE 5-continued

Tumor Delivery Formulations

| | Cationic lipid | carbamate | Phospholipid | lipid-PEG |
|---|---|---|---|---|
| Example 29 | DOTMA | $N^6$-tetrakis(3-aminopropyl)-1,3-propanediamine cholesteryl carbamate | 1,2-dilinoleoyl-sn-glycero-3-phosphoethanolamine | DOPE-PEG 2000 |
| Example 30 | DOTMA | $N^6$-tetrakis(3-aminopropyl)-1,3-propanediamine cholesteryl carbamate | 1,2-dilinoleoyl-sn-glycero-3-phosphoethanolamine | 11.6 mg cholesterol-PEG 660, and 10 mg of DSPE-PEG 2000 |
| Example 31 | DOTMA | $N^6$-tetrakis(3-aminopropyl)-1,3-propanediamine cholesteryl carbamate | 1,2-diarachidonoyl-sn-glycero-3-phosphoethanolamine | cholesterol-PEG 660 |
| Example 32 | DOTMA | $N^6$-tetrakis(3-aminopropyl)-1,3-propanediamine cholesteryl carbamate | 1,2-didocosahexaenoyl-sn-glycero-3-phosphoethanolamine | cholesterol-PEG 660 |

Figure 5A:
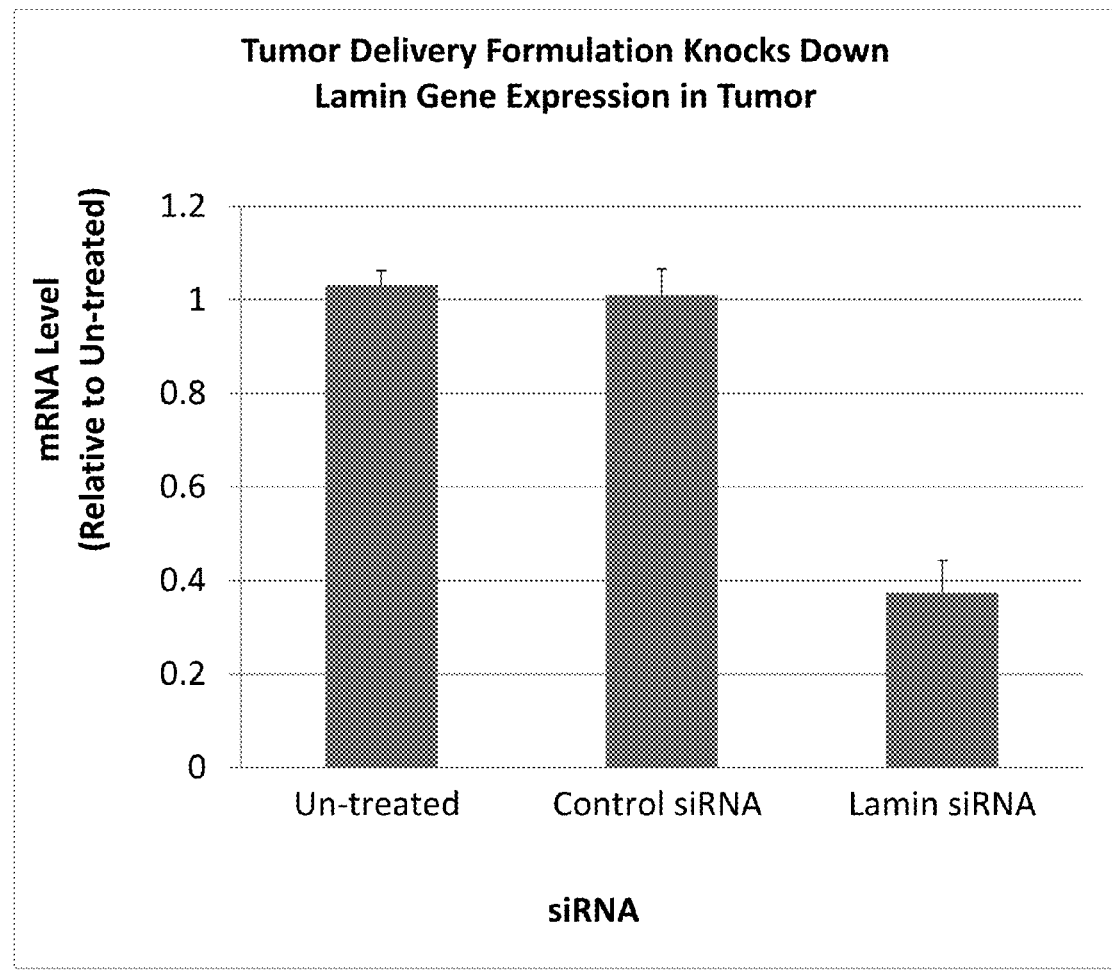
FIG. 5. Balb/C mice were administered 0.2 ml intravenously of a single dose of formulated siRNA at 2 mg/kg. Two days later, the tumor (A) and liver (B) were harvested for analyzing gene expression with real-time RT-PCR method (GAPDH as a reference gene). The tumor model is produced by injecting EMT6 cells (mouse mammary sarcoma original from Balb/C mice) into Glisson capsule of the left lower hepatic lobe. Each data point represents the mean+SEM (n=6).
Figure 5B:
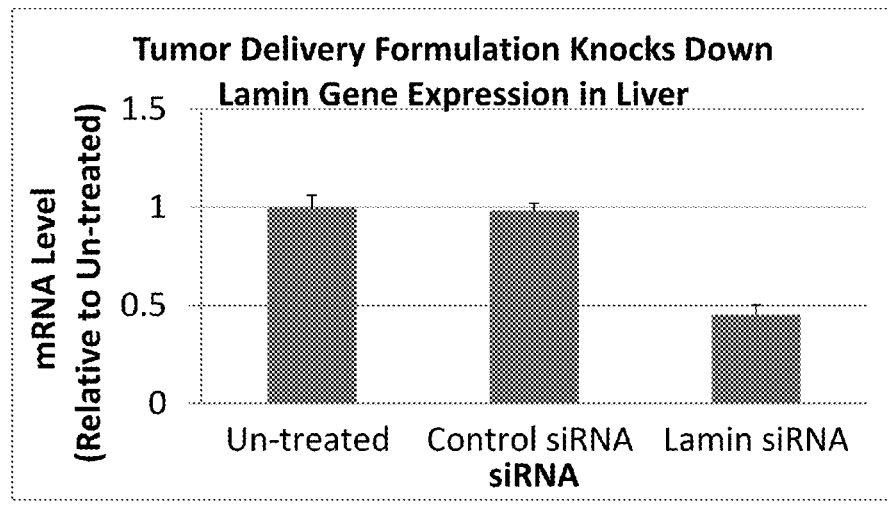

FIG. 5 describes the results of testing a claimed formulation by injection into mice. The results show that injection of lamin siRNA in the formulation of Example 27 is effective in knocking down expression of the corresponding gene in the tumor, but that this formulation changed expression of the gene in liver to a lesser extent.

Example 33

Bone Marrow siRNA Delivery Formulation

A bone marrow siRNA delivery formulation was prepared by the following method. After centrifuging and drying the DOTMA/siRNA salt (containing 1 mg siRNA in complexed with DOTMA) which was made as in Examples 1-4, the salt was re-suspended in 100 μL of chloroform and mixed with the following lipids in chloroform: 6.6 mg $N^6$-tetrakis(3-aminopropyl)-1,3-propanediamine cholesteryl carbamate, 2.2 mg DLinPE (1,2-dilinoleoyl-sn-glycero-3-phosphoethanolamine), 2.4 mg Cholesterol, and 21.6 mg cholesterol-PEG (cholesterol-poly(ethylene glycol)) 660. The mixture was dried under vacuum and stored at 4° C. until use. Before injection, 9% sucrose solution was added with shaking to form an isotonic and a self-emulsifying siRNA/lipid suspension of siRNA/lipid formulation. The formulation was dosed to CD1 mice via tail vein at dose volume of 0.2 ml. Two days later, the mice were sacrificed. The bone marrow and liver were harvested for analyzing gene expression by real-time RT-PCR method.

Example 34

Skin Formulation

A skin siRNA delivery formulation was prepared by the following method. siRNA with or without fluorescently labeled was used for the experiment. The siRNA/DOTMA cationic lipid salt was prepared as the Example 1. Then the siRNA/DOTMA cationic lipid salt was dissolved in 1-octanol. After adding other excipients containing lauroyl glycol and atone, the formulation was applied on the surface of pigskin. After 5 hrs of incubation, the formulations were removed and skin surface was rinsed to remove the unincorporated siRNA. Then the skin tissue was fixed, sectioned (5um thick), stained with DAPI for nuclear stain and examined the florescence intensity under fluorescent microscope.

Example 35

In Vivo Gene Knockdown Examination

All procedures used in animal studies conducted were approved by the Institutional Animal Care and Use Committee (IACUC) and were consistent with local, state and federal regulations as applicable. Mice received siRNA formulations at dose volume of 0.2 ml via tail vein. Mouse tissues were harvested 2 days after dosing and mRNA was isolated with Turbocapture kit (Qiagen) for analyzing change of gene expression with real-time RT-PCR method (SensiMix SYBR One-Step Kit, Bioline).

Example 36

Scale-Up Precipitation of siRNA with Cationic Lipids

To produce a higher amount of precipitates for clinical study of delivery siRNA in vivo, 1 g of ApoB siRNA was solublized in 500 ml of RNase free water completely in room temperature. DOTMA solution was prepared from 2 gram of dry DOTMA dissolved in 25 ml of absolute ethanol. While siRNA solution was stirring on a stirring plate, DOTMA solution was slowly added to the siRNA solution. A precipitate is immediately formed. The mixture was incubated for 20 min at room temperature, then at 4° C. degree for 30 min to several hours. The mixture was centrifuged for 30 min at 30,000 g. The supernatant was removed and the solids were dried under vacuum.

Example 37

Preparation of an Aqueous Solution of the Cationic Lipid DOTMA (N-[1-(2,3-dioleyloxy)propyl]-N,N,N-trimethylammonium chloride) and nucleic acid/DOTMA salts 2 mg DOTMA was dissolved in 0.1 mL of chloroform in a clean, dry borosilicate clear glass vial and the chloroform was evaporated off by blowing nitrogen gas into the vial and any remaining trace amount of chloroform was removed by drying in vacuo in a vacuum chamber. The vial was removed from the vacuum chamber and 1 mL sterilized water was added. The vial was sealed with TEFLON®-lined cap and tightly wrapped with a sealing tape. The vial was vortexed or/and sonicated to clarity.

An aqueous solution containing 1 mg siRNA was added to the aqueous solution of DOTMA. The addition of the siRNA to the aqueous solution of DOTMA cationic lipid caused immediate aggregation forming a water-insoluble cationic lipid/nucleic acid salt comprised of DOTMA and siRNA.

The water-insoluble cationic lipid/nucleic acid salt in a tube was chilled on ice for at least 10 minutes. The water-insoluble cationic lipid/nucleic acid salt in a tube was then centrifuged in an Eppendorf microcentrifuge at maximum speed for 15 minutes to form a pellet. The aqueous layer was carefully removed and the salt pellet was dried in vacuo in a vacuum chamber to remove additional moisture.

Example 38

Preparation of an Aqueous Solution of the Cationic Lipid DOTMA (N-[1-(2,3-dioleyloxy)propyl]-N,N,N-trimethylammonium chloride) and nucleic acid/DOTMA salts The method of Example 35 was performed except that after adding siRNA to DOTMA, the resulting mixture was centrifuged directly without chilling on ice.

Example 39

Preparation of an Aqueous Solution of the Cationic Lipid DOTMA (N-[1-(2,3-dioleyloxy)propyl]-N,N,N-trimethylammonium chloride) and nucleic acid/DOTMA salts The method of Example 36 was performed except that an aqueous solution of DOTMA was added to a siRNA solution.

Example 40

Preparation of an Ethanol Solution of the Cationic Lipid 1,2-Dilinoleyloxy-N,N-dimethylaminopropane (DLinDMA) and nucleic acid/DLinDMA salts The method of Example 35 was performed except that DLinDMA was used as the cationic lipid.

Example 41

Preparation of an Ethanol Solution of the Cationic Lipid N-(1-(2,3-dioleoyloxy)propyl)-N,N,N-trimethylammonium chloride ("DOTAP") and nucleic acid/DOTAP salts The method of Example 35 was performed except that DOTAP was used as the cationic lipid, and this lipid was solubilized in ethanol.

Example 42

Preparation of an Aqueous Solution of the Cationic Lipid DOTMA (N-[1-(2,3-dioleyloxy)propyl]-N,N,N-trimethylammonium chloride) and nucleic acid/DOTMA salts The method of Example 35 was performed except that a bacterial plasmid was used instead of siRNA.

Example 43

Preparation of an Ethanol Solution of the Cationic Lipid DOTMA (N-[1-(2,3-dioleyloxy)propyl]-N,N,N-trimethylammonium chloride) and nucleic acid/DOTMA salts The method of Example 40 was performed except that DOTMA was solubilized in ethanol instead of water.

Example 44

Isolating Nucleic Acid/Cationic Lipid Salts from the Liquid After Mixing Nucleic Acid with Cationic Lipid After mixing with nucleic acid and cationic lipids as the Example 1-4 and 35-41, the mixture was chilled on ice for at least 10 minutes before centrifugation

Example 45

Isolating Nucleic Acid/Cationic Lipid Salts from the Liquid After Mixing Nucleic Acid with Cationic Lipid A nucleic acid and cationic lipid salt was prepared as in Example 42, except that the mixture was dried without centrifuging.

Example 46

Isolating Nucleic Acid/Cationic Lipid Salts from the Liquid After Mixing Nucleic Acid with Cationic Lipid A nucleic acid and cationic lipid salt was prepared as in Example 43, except that the mixture was filtered to collect the precipitated salts.

Example 47

Isolating Nucleic Acid/Cationic Lipid Salts from the Liquid After Mixing Nucleic Acid with Cationic Lipid A nucleic acid and cationic lipid salt was prepared as in Example 42, except the mixture was not chilled before centrifuging.

What is claimed:

1. A composition comprising lipid molecules and polynucleotides, wherein the composition is produced by a method comprising the steps of
   (i) mixing cationic lipids in an alcohol or an aqueous solvent with the polynucleotides in an aqueous solution to form a water-insoluble ionic charge complex of cationic lipids and polynucleotides, (ii) recovering the precipitate from the aqueous solution and drying the precipitate, (iii) completely dissolving the precipitate in an organic solvent or a polar aprotic solvent to produce a first solution, (iv) dissolving colipids in an organic solvent or a polar aprotic solvent to produce a second solution, (v) mixing the first solution with the second solution, and (vi) removing the solvent from the solution produced by step (v)

wherein the organic solvent of steps (iii) and (iv) is independently selected from the group consisting of an alcohol, dichloromethane, chloroform, THF, DMSO, dimethylacetamide, and lauroyl glycol.

2. The composition of claim 1, wherein the molar charge ratio of the polynucleotides to the cationic lipids in the precipitate of step (ii) is 1:1.

3. The composition of claim 1, wherein the organic or polar aprotic solvent of steps (iii) and (iv) comprises ethanol, dimethylacetamide, dimethylformamide, N-methyl pyrrolidine, chloroform, dichloromethane, methylene chloride, or a cyclic ether.

4. The composition of claim 1, wherein the cationic lipid molecules are selected from the group consisting of N,N-dioleyl-N,N-dimethylammonium chloride (DODAC); N-(1-(2,3-dioleyloxyl)propyl)-N,N,N-trimethylammonium chloride (DOTMA); N,N-dimethyl-(2,3-dioleyloxyl) propylamine ("DODMA"); N,N-distearyl-N,N-dimethylammonium bromide ("DDAB"); N-(1-(2,3-dioleoyloxy)propyl)-N,N,N-trimethylammonium chloride ("DOTAP"); 3-(N—(N',N'-dimethylaminoethane)-carbamoyl)cholesterol (DC-Chol); N-(1,2-dimyristyloxyprop-3-yl)-N,N-dimethyl-N-hydroxyethyl ammonium bromide ("DMRIE"); 1,2-Dilinoleyloxy-N,N-dimethylaminopropane (DLinDMA); and 1,2-Dilinolenyloxy-N,N-dimethylaminopropane (DLenDMA), dioctadecyldimethylammonium (DODMA), distearyldimethylammonium (DSDMA), 1,2-dilinoleyloxy-N,N-dimethylaminopropane (DLinDMA), 1,2-dilinolenyloxy-N,N-dimethylaminopropane (DLenDMA), $N^4$-spermine cholesteryl carbamate (GL-67), $N^4$-spermidine 3hytosterol carbamate (GL-53), 1-($N^4$-spermine)-2,3-dilaurylglycerol carbamate (GL-89) and mixtures thereof.

5. The composition of claim 1, wherein the cationic lipid molecules are selected from the group consisting of N-(1-(2,3-dioleoyloxy)propyl)-N,N,N-trimethylammonium chloride, 1,2-dimyristoyl-3-dimethylammonium propane, 1,2-dilinoleyloxy-N,N-dimethylaminopropane, 3-(N—(N',N'-dimethylaminoethane)-carbamoyl)cholesterol, and N-(1-(2,3-dioleyloxyl)propyl)-N,N,N-trimethylammonium chloride.

6. The composition of claim 1, wherein the nucleic acid is selected from the group consisting of DNA, RNA, antisense, aptamer, antagomir, plasmid, interfering nucleic acid (iNA), ribozyme, small interfering nucleic acid (siRNA), microRNA (miRNA), and mixtures thereof.

7. The composition of claim 1, wherein the colipids comprise a carbamate.

8. The composition of claim 7, wherein the carbamate is selected from the group consisting of Formulas I-IV

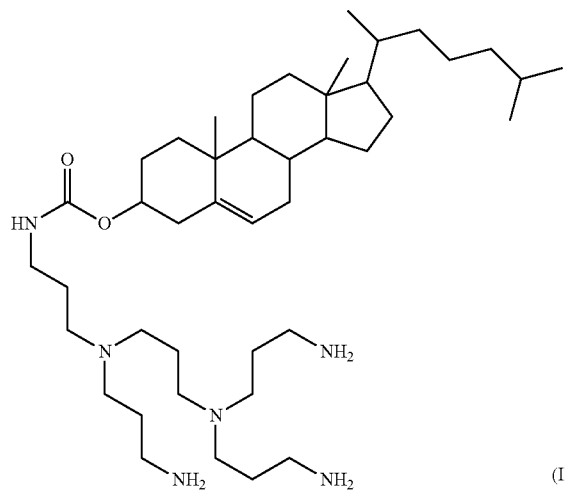

(I)

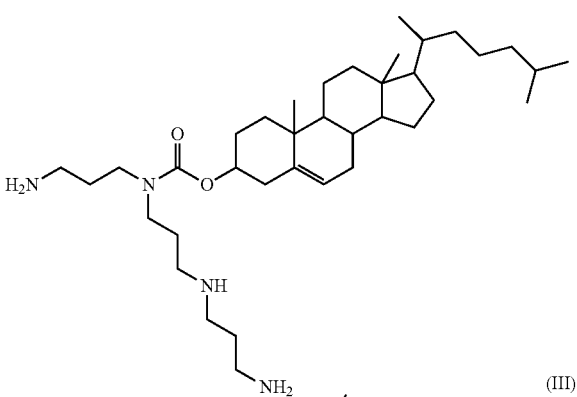

(II)

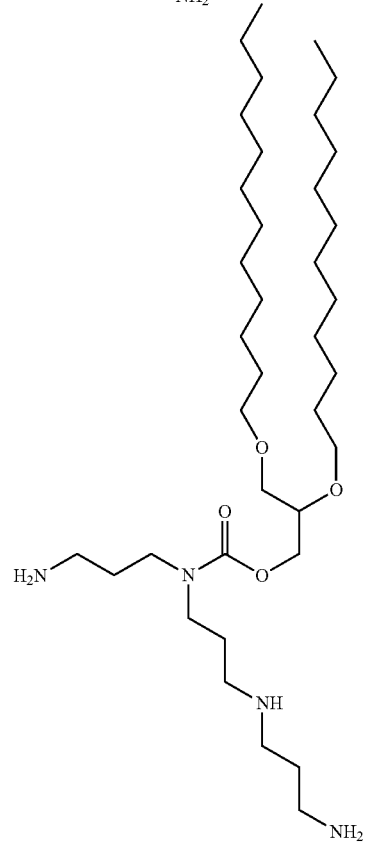

(III)

(IV)

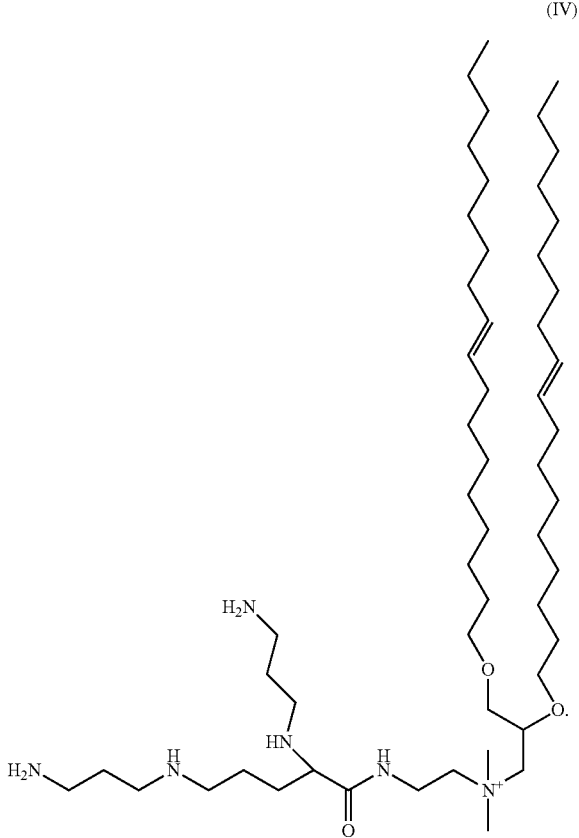

9. The composition of claim 1, wherein the colipids comprise a neutral phospholipid.

10. The composition of claim 9, wherein the phospholipid is selected from the group consisting of phosphatidyl ethanolamine, phosphatidyl choline, phosphatidyl inositol, sphingomyelin, and diphosphatidyl glycerol.

11. The composition of claim 9, wherein the phospholipid comprises 8-22 carbon alkyl chains.

12. The composition of claim 11, wherein the alkyl chains are selected from a group consisting of 18:2, 20:4, and 22:6 alkyl chains.

13. The composition of claim 1, wherein the colipids comprise a sterol.

14. The composition of claim 13, wherein the sterol is selected from the group consisting of cholesterol, lanosterol, 24-isopropylcholesterol, nicasterol, 7-dehydrocholesterol, 24-dehydrocholesterol, gorgosterol, dinosterol, 24S-hydroxycholesterol, a phytosterol, ergosterol, stigmasterol, campesterol, fucosterol, β-sitosterol, a phytostanol, a sterol ester, a steryl glycoside, and a steryl alkyl ether.

15. The composition of claim 1, wherein the colipids comprise a sterol-PEG compound.

16. The composition of claim 15, wherein the sterol of the sterol-PEG compound is selected from the group consisting of a cholesterol, lanosterol, 24-isopropylcholesterol, nicasterol, 7-dehydrocholesterol, 24-dehydrocholesterol, gorgosterol, dinosterol, 24S-hydroxycholesterol, a phytosterol, ergosterol, stigmasterol, campesterol, fucosterol, β-sitosterol, a phytostanol, a sterol ester, a steryl glycoside, and a steryl alkyl ether.

17. The composition of claim 15, wherein the PEG of the sterol-PEG compound has a molecular weight between 200 and 5000 kDa.

18. The composition of claim 1, wherein the colipids comprise one or more lipids selected from the group consisting of cholesterol, cholesterol PEG, PE, and N 6-tetrakis(3-aminopropyl)-1,3-propanediamine cholesteryl carbamate (Formula I).

19. The composition of claim 1, wherein the colipids consist, or every 1 part polynucleotide, 4.4 parts N 6-tetrakis(3-aminopropyl)-1,3-propanediamine cholesteryl carbamate (Formula I)/2.7-4.4 parts PE/14.4 parts cholesterol PEG/1.6 parts cholesterol (weight/weight).

20. A composition of claim 1, wherein the colipids comprise 1,2-dilinoleoyl-sn-glycero-3-phosphoethanolamine, cholesterol, and cholesterol-PEG.

21. The composition of claim 1, further comprising an aqueous solvent and one or more colipids, wherein the colipids are selected from the group consisting of lipid carbamates, phospholipids, sterols and sterol-PEG compounds, and wherein the composition is produced by a method further comprising the step of
(vii) adding the aqueous solvent to form a self-emulsifying suspension of lipid and nucleic acid, wherein the suspension consists of a monodisperse particle size distribution of under 400 nm,
wherein the composition is suitable for administration to a subject.

22. The composition of claim 21, wherein the composition aqueous solvent further comprises pharmaceutically acceptable carriers.

* * * * *